United States Patent
Bleisch et al.

(10) Patent No.: US 9,550,774 B2
(45) Date of Patent: Jan. 24, 2017

(54) DIHYDROPYRIDO PYRIMIDINE COMPOUNDS AS AUTOTAXIN INHIBITORS

(71) Applicant: Eli Lilly and Company, Indianapolis, IN (US)

(72) Inventors: Thomas John Bleisch, Noblesville, IN (US); Robert Anthony Doti, Indianapolis, IN (US); Lance Allen Pfeifer, Carmel, IN (US); Bryan Hurst Norman, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/761,009

(22) PCT Filed: Apr. 4, 2014

(86) PCT No.: PCT/US2014/032946
§ 371 (c)(1),
(2) Date: Jul. 15, 2015

(87) PCT Pub. No.: WO2014/168824
PCT Pub. Date: Oct. 16, 2014

(65) Prior Publication Data
US 2015/0368240 A1   Dec. 24, 2015

Related U.S. Application Data

(60) Provisional application No. 61/811,280, filed on Apr. 12, 2013, provisional application No. 61/811,290, filed on Apr. 12, 2013.

(51) Int. Cl.
*A61K 31/519* (2006.01)
*C07D 471/04* (2006.01)

(52) U.S. Cl.
CPC .................... *C07D 471/04* (2013.01)

(58) Field of Classification Search
CPC ...................................... C07D 471/04
See application file for complete search history.

(56) References Cited

U.S. PATENT DOCUMENTS 7,524,852 B2   4/2009   Arai et al.

FOREIGN PATENT DOCUMENTS

| WO | 01/32632 | 5/2001 |
| WO | 2011/048477 | 4/2011 |
| WO | 2012/085167 | 6/2012 |

*Primary Examiner* — Brian McDowell
(74) *Attorney, Agent, or Firm* — Macharri R. Vorndran-Jones

(57) ABSTRACT

The present invention provides compounds of the formula (I) or a pharmaceutically acceptable salt thereof. Compounds of the invention are autotaxin inhibitors useful in the treatment of pain associated with osteoarthritis.

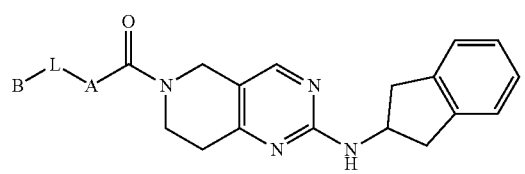

14 Claims, No Drawings

DIHYDROPYRIDO PYRIMIDINE COMPOUNDS AS AUTOTAXIN INHIBITORS

This invention relates to dihydropyrido pyrimidine compounds, or pharmaceutically acceptable salts thereof, and therapeutic use thereof. Compounds of this invention are autotaxin inhibitors.

Autotaxin is an enzyme reported to be the primary source of extracellular lysophosphatidic acid (LPA), which up-regulates pain-related proteins through one if its cognate receptors, $LPA_1$. LPA is an intracellular lipid mediator which influences a multiplicity of biological and biochemical processes. Targeted inhibition of autotaxin-mediated LPA biosynthesis may provide a novel mechanism to prevent pain. Compounds that inhibit autotaxin are desired.

Pain associated with osteoarthritis (OA) is reported to be the primary symptom leading to lower extremity disability in OA patients. Over 20 million Americans have been diagnosed with OA, the most common of the arthropathies. There is a desire for treatment options for patients suffering from pain associated with OA.

U.S. Pat. No. 7,524,852 ('852) discloses certain substituted bicyclic pyrimidine derivatives as anti-inflammatory agents.

Certain indole compounds having autotaxin activity are disclosed in PCT/US2011/048477.

The present invention provides novel compounds which are autotaxin inhibitors. The present invention provides certain novel compounds that inhibit the autotaxin mediated production of LPA. Autotaxin inhibitor compounds are desired to provide treatments for autotaxin mediated conditions, such as pain associated with OA.

The present invention provides compounds of Formula I

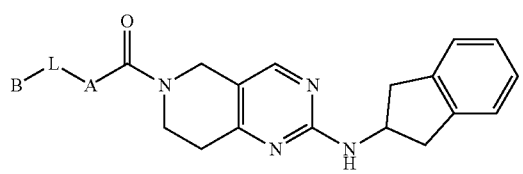

I wherein
A is selected from the group consisting of

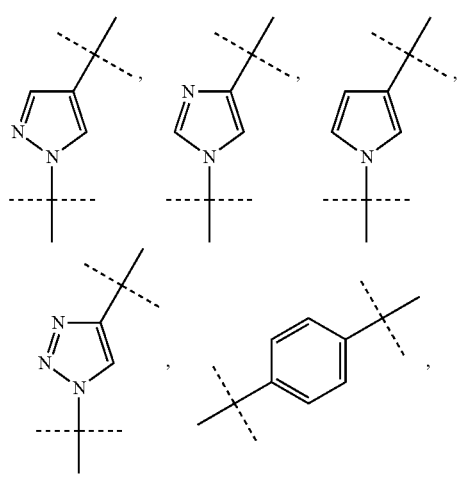

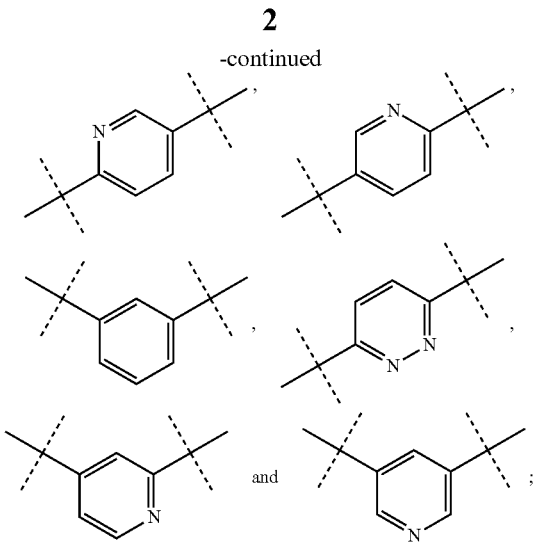

L is a bond or $C_1$-$C_3$ alkyl; and
B is selected from the group consisting of H,

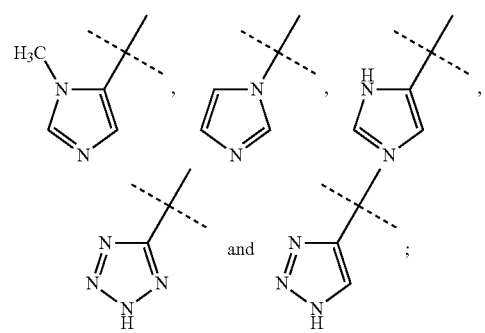

or a pharmaceutically acceptable salt thereof.

It is preferred that B is selected from the group consisting of

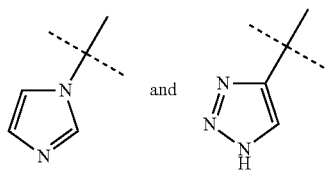

A compound of the invention wherein B is

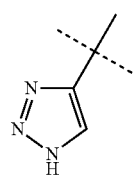

is further preferred.

In a preferred aspect of the present invention, A is selected from the group consisting of

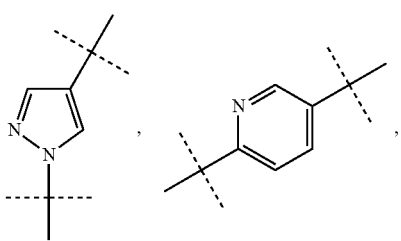

It is preferred that A is selected from the group consisting of

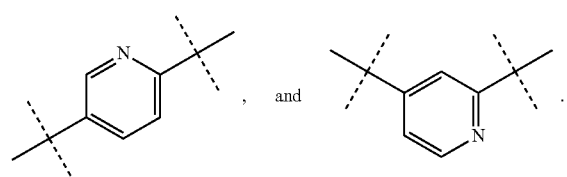

It is preferred that A is

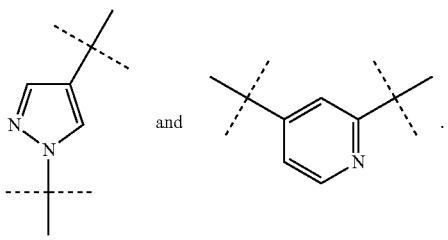

In another embodiment A is

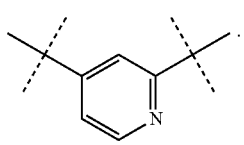

It is a preferred aspect of the present invention that L is selected from the group consisting of a bond and CH$_2$. It is preferred that L is a bond. It is preferred that L is CH$_2$.

The present invention provides a compound of Formula II

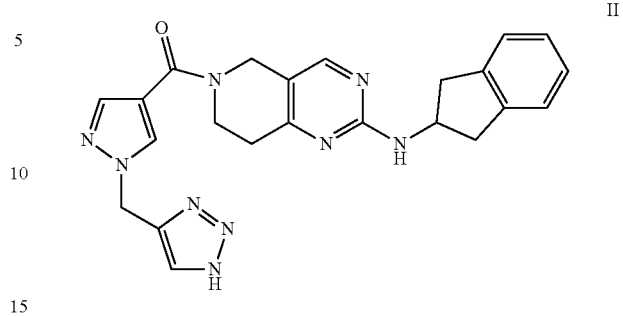

or a pharmaceutically acceptable salt thereof.

The present invention provides a compound of Formula III

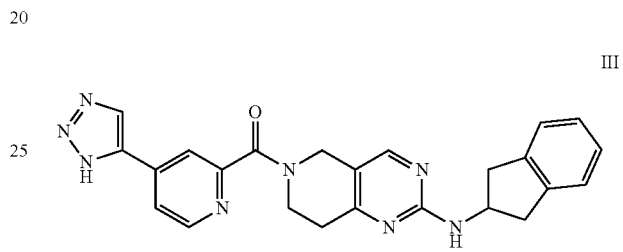

or a pharmaceutically acceptable salt thereof.

It is understood that compounds of the present invention may exist as tautomeric forms. When tautomeric forms exist, each form and mixtures thereof, are contemplated in the present invention.

The present invention also provides a method of treating pain associated with OA in a patient, comprising administering to a patient in need of such treatment an effective amount of a compound of Formula I, or a pharmaceutically acceptable salt thereof.

This invention provides a compound of Formula I, or a pharmaceutically acceptable salt thereof, for use in therapy.

This invention provides a compound of Formula I, or a pharmaceutically acceptable salt thereof, for use in for the treatment of pain associated with OA. Even furthermore, this invention provides the use of a compound of Formula I, or a pharmaceutically acceptable salt thereof, for the manufacture of a medicament for the treatment of pain associated with OA.

The invention further provides a pharmaceutical composition, comprising a compound of Formula I, or a pharmaceutically acceptable salt thereof, and one or more pharmaceutically acceptable carriers, diluents, or excipients. In one embodiment, the composition further comprises one or more other therapeutic agents. The invention also encompasses novel intermediates and processes for the synthesis of the compounds of Formula I.

The term "pharmaceutically-acceptable salt" refers to a salt of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "treating" (or "treat" or "treatment") as used herein refers to restraining, slowing, stopping, or reversing the progression or severity of an existing symptom, condition, or disorder. Symptoms, conditions, or disorders may present as "acute" or "chronic" events. In an acute event a compound is administered at the onset of symptom, condition, or disorder and discontinued when the event disappears. A chronic event is treated during the course of the disorder or condition associated with the symptom or event, wherein the chronic treatment is not dependent on a particular manifestation of the symptom or event. The present invention contemplates both acute and chronic treatment.

Compounds of the present invention inhibit autotaxin, and are useful for treating a disease or condition associated with an increase in autotaxin. Compounds of the present invention inhibit the autotaxin mediated production of LPA and are useful for treating a disease or condition accompanied by an increase in LPA. Compounds of this invention inhibit autotaxin mediated LPA biosynthesis when compared to other LPA lipid mediators. Compounds of this invention are useful for treating a disease or condition associated with an increase in LPA.

As used herein, "patient" refers to an animal in need of treatment. A preferable embodiment is a patient that is a mammal, which is preferably a human. Another preferable embodiment is a patient that is a companion animal such as a dog, cat, or a fowl.

As used herein, the term "effective amount" refers to the amount or dose of compound of the invention or a pharmaceutically acceptable salt thereof which upon single or multiple dose administration to the patient, provides the desired effect in the patient under diagnosis or treatment. It will be understood that the amount of active agent actually administered will be determined by a physician, in light of the relevant circumstances, including the condition to be treated, the chosen route of administration, the actual active agent administered, the age, weight, and response of the individual patient, and the severity of the patient's symptoms and other relevant circumstances.

A compound of the present invention is preferably formulated as pharmaceutical compositions administered by any route which makes the compound bioavailable. Most preferably, such compositions are for oral administration. Such pharmaceutical compositions and processes for preparing same are well known in the art. See, e.g., *Remington: The Science and Practice of Pharmacy* (D. B. Troy, Editor, 21st Edition, Lippincott, Williams & Wilkins, 2006).

Generally, a compound of formula I may be prepared from a compound of formula IV. More specifically in Scheme A, a compound of formula IV is coupled with a compound of formula VII in the presence of O-benzotriazol-1-yl-N,N,N',N'-tetramethyluronium tetrafluoroborate and a base such as diisopropylethylamine to provide a compound of formula I. Suitable solvents include dimethyl sulfoxide.

Alternatively in Scheme A, a compound of formula I may be prepared from a compound of formula V. More specifically, a compound of formula IV is coupled with a compound of formula VIII where Pc is a suitable precursor to the group B in the presence of 1-(3-dimethylaminopropyl)-3-ethylcarbodiimide hydrochloride and a base such as N,N-dimethyl-4-pyridinamine to provide a compound of formula V. Suitable solvents include dichloromethane. A compound of formula V where Pc is a suitable precursor the group B is reacted under conditions as described in the Examples and Preparations to provide a compound of formula I. The skilled medicinal chemist will select a value of Pc appropriate for conversion to the group B. A compound of formula VIII where Pc is a suitable precursor to the group B may be prepared as described in the Examples and Preparations.

Scheme A

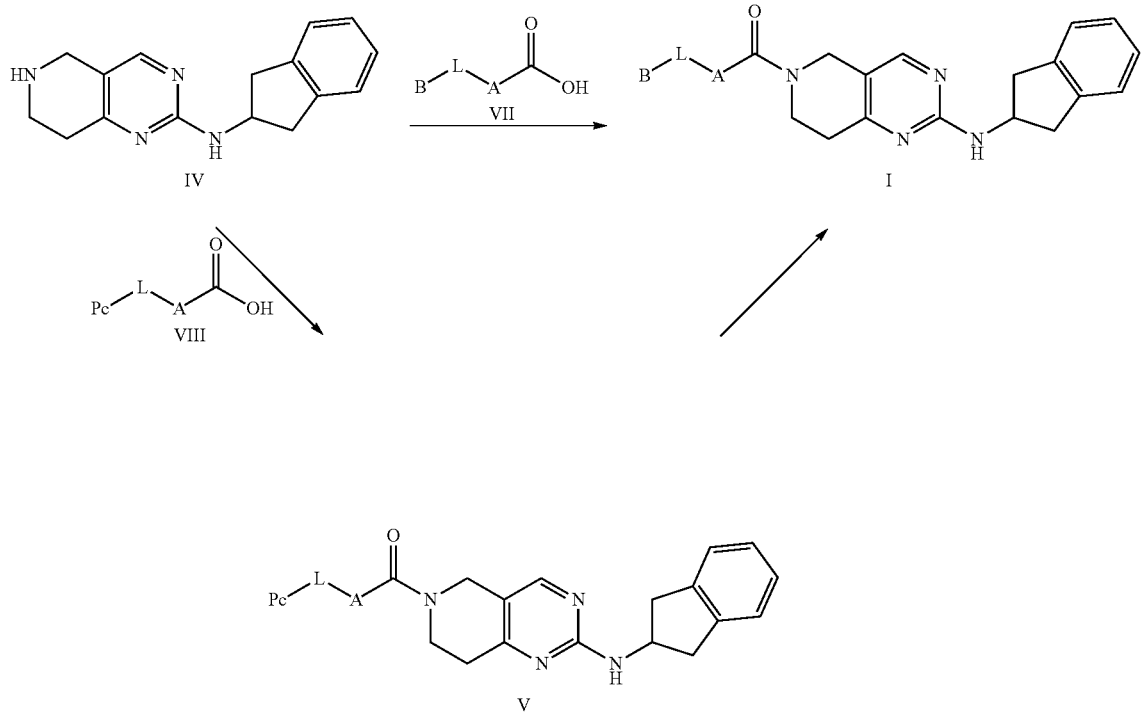

As shown in Scheme B, a compound of formula IV may be prepared from a compound of formula VI where Pg is an amine protecting group. More specifically, a compound of formula VI where Pg is tert-butoxycarbonyl is reacted with an acid such as hydrochloric acid in a solvent such as tetrahydrofuran to provide a compound of formula IV.

Scheme B

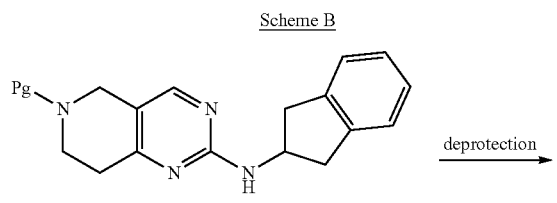

In Scheme C, a compound of formula VI where Pg is tert-butoxycarbonyl may be prepared from a compound of formula IX. More specifically, N-tert-butoxycarbonyl-4-piperidone is reacted sequentially with $(CH_3)_2NCH(OCH_3)_2$ in a solvent such as dimethylformamide, and then with a compound of formula IX, a base such as potassium carbonate in a co-solvent such as ethanol to provide a compound of formula VI where Pg is tert-butoxycarbonyl. A compound of formula IX may be prepared by reacting 2,3-dihydro-1H-inden-2-amine hydrochloride and 1H-pyrazole-1-carboximidamide hydrochloride with a base such as diisopropylethylamine in a solvent as acetonitrile.

Scheme C

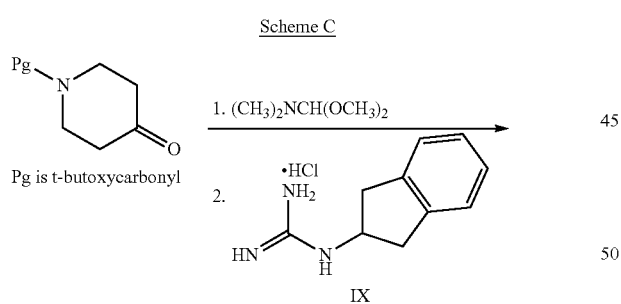

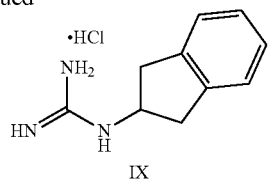

IX

PREPARATIONS AND EXAMPLES

The following Preparations and Examples further illustrate the invention and represent a typical synthesis of the compounds of the invention. It should be understood that the Preparations and Example are set forth by way of illustration and not limitation, and that various modifications may be made by one of ordinary skill in the art. The reagents and starting materials are generally available to one of ordinary skill in the art. Others may be prepared by standard techniques of organic and heterocyclic chemistry which are analogous to the synthesis of known structurally similar compounds and procedures described by the Preparations and Example which follow, including any novel procedures.

Unless noted to the contrary, the compounds illustrated herein are named and numbered using either ACDLABS or Symyx Draw 3.2.

Preparation 1

Synthesis of 1-indan-2-ylguanidine hydrochloride

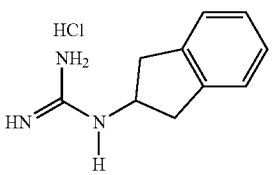 [SMILES: N=C(N)NC1Cc2ccccc2C1 ; Cl]

Stir a solution of 2,3-dihydro-1H-inden-2-amine hydrochloride (197 g; 1.08 equiv; 1.16 moles), 1H-pyrazole-1-carboximidamide hydrochloride (158 g; 1.00 equiv; 1.08 moles) and diisopropylethylamine (400 g; 2.87 equiv; 3.09 moles; 539.74 mL) in acetonitrile (2 L) at 62° C. for 2 hours, during which time a white solid precipitates. Cool the mixture to 25° C., then filter and wash with 300 mL acetonitrile and 300 mL methyltert-butyl ether. Dry the product in air at 25° C. for 1 h to afford the title compound (200 g, 87%) as a white solid. MS (m/z): 176 (M+1).

Preparation 2

Synthesis of tert-butyl 2-(indan-2-ylamino)-7,8-dihydro-5H-pyrido[4,3-d]pyrimidine-6-carboxylate Stir a solution of 1,1-dimethoxy-N,N-dimethyl-methanamine (224 g; 2.15 equiv; 1.88 moles; 250.98 mL) and N-t-butoxycarbonyl-4-piperidone (250 g; 1.44 equiv; 1.25 moles) in dimethylformamide (1.2 L) at 109° C. under N₂ for 4 h. Cool the mixture to 25° C. and then add ethanol (700 mL; 12.02 moles; 553.91 g). Add 1-indan-2-ylguanidine hydrochloride (185 g; 1.00 equiv; 873.90 mmoles) and potassium carbonate (475 g; 3.44 moles) to the mixture at 25° C. in one portion to form a white suspension. Stir the mixture at 80-90° C. for 24 h, then cool to 25° C. and pour the mixture into 5 L ice/water to get a yellow suspension. Extract with ethyl acetate (3×3 L), and wash the organic layer with 10% lithium chloride solution (3 L), water (3 L), and saturated sodium chloride solution (3 L). Dry over anhydrous sodium sulfate, filter and concentrate to give about 300 ml of a red solution. Filter the solution through a silica gel plug (10 cm height, 5 cm diameter) and then concentrate to dryness to give the title compound as a red gel (320 g, 100%). MS (m/z): 367 (M+1).

Preparation 3

Synthesis of N-indan-2-yl-5,6,7,8-tetrahydropyrido[4,3-d]pyrimidin-2-amine

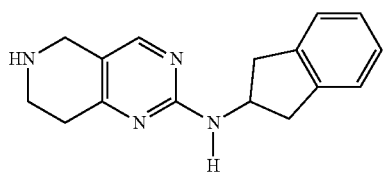 [SMILES: c1ccc2c(c1)CC(Nc1ncc3c(n1)CCNC3)C2]

Add portion wise hydrochloric acid (900 mL; 5M in water; 5.17 equiv; 4.50 mole; 1.08 kg) to a solution of tert-butyl 2-(indan-2-ylamino)-7,8-dihydro-5H-pyrido[4,3-d]pyrimidine-6-carboxylate (319 g; 1.00 equiv; 870.48 mmoles) in tetrahydrofuran (1.5 L). Once the addition is complete, stir the solution at 50° C. for 1 h. Cool the mixture to 25° C. and then add 3 L methyltert-butyl ether and 1 L water. Allow the solution to stand at 20° C. for 16 h. Separate the phases and extract the aqueous phase with dichloromethane (2 L). Discard the organic extracts and adjust the aqueous phase to pH 10 using 4M sodium hydroxide. Extract with ethyl acetate (3×3 L), and wash the combined organic extracts with saturated sodium chloride (2 L). Dry over anhydrous sodium sulfate, filter and concentrate to dryness to give a red gel. Redissolve the substance in ethyl acetate (300 mL) and petroleum ether (200 mL) at 50° C., and allow for precipitation over 24 hours. Filter and dry to afford the title compound (85 g, 37%). MS (m/z): 267 (M+1).

Preparation 4

Synthesis of ethyl-1-(3-trimethylsilylprop-2-ynyl)pyrazole-4-carboxylate

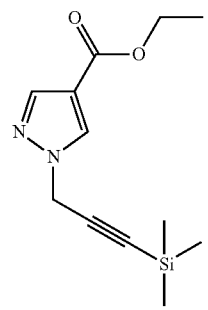 [SMILES: CCOC(=O)c1cnn(CC#C[Si](C)(C)C)c1]

Place ethyl-1H-pyrazole-4-carboxylate (700.7 mg, 5 mmoles) in a 50 mL round bottom flask and dissolve in dimethylformamide (11 mL). Cool the reaction mixture to 0° C. Add sodium hydride (180.0 mg, 4.5 mmoles) portion wise over 20 minutes. Stir the reaction mixture for 20 minutes and then add 3-bromoprop-1-ynyl(trimethyl)silane (0.92 mL, 6.5 mmoles) and stir for an additional 30 minutes. Quench the reaction mixture with water (20 mL) and extract three times with ethyl acetate and discard the aqueous phase. Combine and wash the organic layers one time with brine. Dry over sodium sulfate, filter and concentrate under reduced pressure. Purify the residue by flash silica gel chromatography with ethyl acetate/hexane to give the title compound (0.75 g, 60%). LCMS (m/z): 251.0 (M+1).

Preparation 5

Synthesis of ethyl-1-(1H-triazol-4-ylmethyl)pyrazole-4-carboxylate

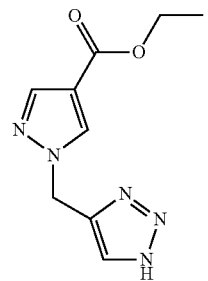 [SMILES: CCOC(=O)c1cnn(Cc2c[nH]nn2)c1]

Place ethyl-1-(3-trimethylsilylprop-2-ynyl)pyrazole-4-carboxylate (0.751 g, 3.00 mmoles) in a microwave vial and dissolve in dimethylformamide (12.00 mL) and water (18 mL). Add copper(II)sulfate pentahydrate (149.79 mg, 0.6 mmoles) and L-ascorbic acid sodium salt (1.19 g, 6.00 mmoles) and dimethylformamide (2 mL). Degas the reaction mixture three times. Add azidotrimethylsilane (1.60 mL, 12.00 mmoles) and heat at 90° C. for 15 hours. Cool the mixture to room temperature, extract three times with ethyl acetate and discard the aqueous phase. Combine and wash the organic layers one time with brine. Dry over sodium sulfate, filter and concentrate under reduced pressure. Purify the residue by flash silica gel chromatography with methanol/acetonitrile to give the title compound (0.5 g, 75%). LCMS (m/z): 222.0 (M+1).

Preparation 6

Synthesis of 1-(1H-triazol-4-ylmethyl)pyrazole-4-carboxylic acid

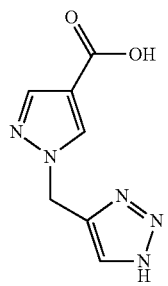 [SMILES: O=C(O)c1cnn(Cc2c[nH]nn2)c1]

Place ethyl 1-(1H-triazol-4-ylmethyl)pyrazole-4-carboxylate, (2.1 g, 7.16 mmoles) in a 100 mL round bottom flask and dissolve in tetrahydrofuran (30 mL) and water (15 mL). Add lithium hydroxide (1.50 g, 35.79 mmoles) and heat at 55° C. for 18 hours. Dilute the reaction mixture with 5 N hydrochloric acid to pH 1-2. Remove the solvent under reduced pressure. Add ethanol and filter away the solid. Concentrate the filtrate under reduced pressure to give the title compound (3.01 g, 105%). LCMS (m/z): 194.0 (M+1).

Example 1

Synthesis of [2-(indan-2-ylamino)-7,8-dihydro-5H-pyrido[4,3-d]pyrimidin-6-yl]-[1-(1H-triazol-4-ylmethyl)pyrazol-4-yl]methanone An alternative chemical name for the compound of Example 1 is [2-(2,3-dihydro-1H-inden-2-ylamino)-7,8-dihydropyrido[4,3-d]pyrimidin-6(5H)-yl][1-(1H-1,2,3-triazol-4ylmethyl)-1H-pyrazol-4-yl]methanone.

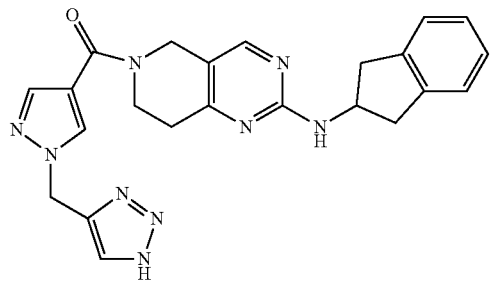 [SMILES: O=C(c1cnn(Cc2c[nH]nn2)c1)N1CCc2nc(NC3Cc4ccccc4C3)ncc2C1]

Place 1-(1H-triazol-4-ylmethyl)pyrazole-4-carboxylic acid (2.28 g 5.70 mmoles) in a 100 mL round bottom flask and dissolve in dimethyl sulfoxide (28.5 mL). Add diisopropylethylamine (6.8 mL, 39.2 mmoles) and O-benzotriazol-1-yl-N,N,N',N'-tetramethyluronium tetrafluoroborate (3.5 g, 11.00 mmoles), and stir for 10 minutes. Add N-indan-2-yl-5,6,7,8-tetrahydropyrido[4,3-d]pyrimidin-2-amine (1.52 g, 5.70 mmoles) and stir the reaction mixture for 90 minutes. Quench the reaction with water (40 mL) and extract three times with 10% methanol/ethyl acetate and discard the aqueous phase. Combine and wash the organic layers one time with brine. Dry over sodium sulfate, filter and concentrate under reduced pressure. Purify the residue by reverse phase chromatography and crystallize with methanol/ethyl acetate/hexane to give the title compound (0.45 g, 18%). LCMS (m/z): 442.2 (M+1).

Preparation 7

Synthesis of [2-(indan-2-ylamino)-7,8-dihydro-5H-pyrido[4,3-d]pyrimidin-6-yl]-(1H-pyrazol-4-yl)methanone

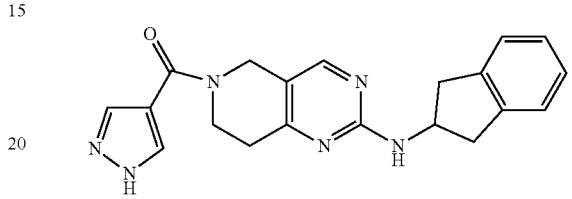

Place 4-pyrazolecarboxylic acid (700.7 mg, 5 mmoles), N-indan-2-yl-5,6,7,8-tetrahydropyrido[4,3-d]pyrimidin-2-amine (2.00 g, 7.51 mmoles), 1-(3-dimethylaminopropyl)-3-ethylcarbodiimide hydrochloride (2.16 g, 11.26 mmoles), and 4-pyridinamine, N,N-dimethyl (45.9 mg, 0.3 mmoles) in a 250 mL round bottom flask and dissolve in dichloromethane (60 mL). Stir the reaction mixture for 18 hours at 25° C. Quench the reaction with saturated sodium bicarbonate (50 mL) and extract two times with dichloromethane. Dry over sodium sulfate, filter and concentrate under reduced pressure. The residue is recrystallized from methanol/ethyl acetate to give the title compound (0.98 g, 28%). LCMS (m/z): 361.2 (M+1).

Preparation 8

Synthesis of 1H-imidazol-4-yl-[2-(indan-2-ylamino)-7,8-dihydro-5H-pyrido[4,3-d]pyrimidin-6-yl]methanone

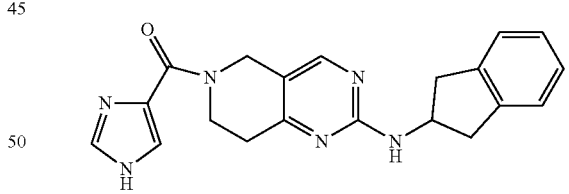

Place 1H-imidazole-4-carboxylic acid (1.26 g, 11.21 mmoles), 1-hydroxybenzotriazole monohydrate (1.14 g, 7.45 mmoles), N-indan-2-yl-5,6,7,8-tetrahydropyrido[4,3-d]pyrimidin-2-amine (1.82 g, 6.83 mmoles), triethylamine (2.84 mL, 20.36 mmoles), and 1-(3-dimethylaminopropyl)-3-ethylcarbodiimide hydrochloride (1.43 g, 7.45 mmoles) in a round bottom flask. Add dimethylformamide (22 mL) and stir overnight at 25° C. Quench the reaction with water and extract with 9:1 dichloromethane/methanol. Wash one time with water and dry over sodium sulfate, filter and concentrate under reduced pressure. The residue is purified by normal phase chromatography using methanol/dichloromethane to give the title compound (1.2 g, 49%). LCMS (m/z): 361.2 (M+1).

Preparation 9

Synthesis of [2-(indan-2-ylamino)-7,8-dihydro-5H-pyrido[4,3-d]pyrimidin-6-yl]-(1H-pyrrol-3-yl)methanone

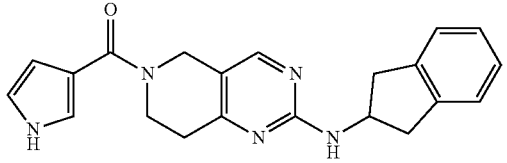 [SMILES: O=C(c1cc[nH]c1)N1CCc2nc(NC3Cc4ccccc4C3)ncc2C1]

Place N-indan-2-yl-5,6,7,8-tetrahydropyrido[4,3-d]pyrimidin-2-amine (1.08 g, 4.05 mmoles), 1H-pyrrole-3-carboxylic acid (500.00 mg, 4.50 mmoles) in a round bottom flask. Add dimethylformamide (15 mL) and diisopropylethylamine (3.14 mL, 18.00 mmoles; 3.14). Cool to 0° C. and add 1-propanephosphonic acid cyclic anhydride (3.45 mL, 5.85 mmoles) dropwise. Stir at 0° C. and allow to warm to room temperature and stir at 25° C. for 18 hours. Pour into ice water and stir for 15 minutes. Filter the solid, wash with water, and dry solid in vacuum oven at 40° C. to give the title compound (1.62 g, 31%). LCMS (m/z): 360.2 (M+1).

Preparation 10

Synthesis of [2-(indan-2-ylamino)-7,8-dihydro-5H-pyrido[4,3-d]pyrimidin-6-yl]-(1-prop-2-ynylpyrrol-3-yl)methanone

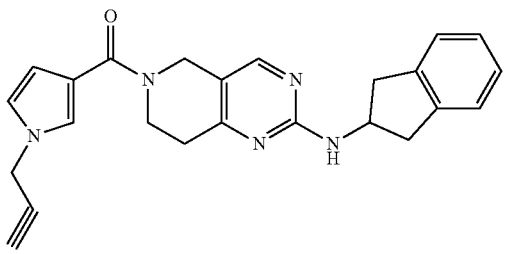 [SMILES: C#CCn1ccc(C(=O)N2CCc3nc(NC4Cc5ccccc5C4)ncc3C2)c1]

Place [2-(indan-2-ylamino)-7,8-dihydro-5H-pyrido[4,3-d]pyrimidin-6-yl]-(1H-pyrrol-3-yl)methanone (500 mg, 1.39 mmoles) and dimethylformamide (3 mL) in a round bottom flask and cool to ° C. Add sodium bis(trimethylsilyl)amide (1.81 mL, 1.81 mmoles) and stir for 40 minutes. Add 3-bromoprop-1-ynyl(trimethyl)silane (216.50 µL, 1.53 mmoles). Quench the reaction with water and extract three times with ethyl acetate. Wash one time with brine and dry over sodium sulfate, filter and concentrate under reduced pressure. The residue is purified by normal phase chromatography using methanol/dichloromethane to give the title compound (0.55 g, 25%). LCMS (m/z): 398.0 (M+1).

Preparation 11

Synthesis of methyl 1-(3-trimethylsilylprop-2-ynyl)triazole-4-carboxylate

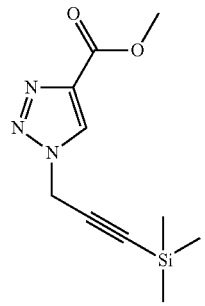 [SMILES: COC(=O)c1cn(CC#C[Si](C)(C)C)nn1]

Place methyl 1H-triazole-5-carboxylate (400.00 mg, 3.15 mmoles) and dimethylformamide (6.84 mL) in a round bottom flask. Cool the mixture to 0° C. Add sodium hydride (120.00 mg, 3.0 mmoles) portionwise over 20 minutes and then stir for 20 minutes. Add 3-bromoprop-1-ynyl(trimethyl)silane (578.83 µL, 4.09 mmoles). Quench the reaction with water and extract three times with ethyl acetate. Wash one time with brine and dry over sodium sulfate, filter and concentrate under reduced pressure. The residue is purified by normal phase chromatography using ethyl acetate/hexane to give the title compound (0.25 g, 33%). LCMS (m/z): 238.0 (M+1).

Preparation 12

Synthesis of methyl 1-[(5-trimethylsilyl-1H-triazol-4-yl)methyl]triazole-4-carboxylate

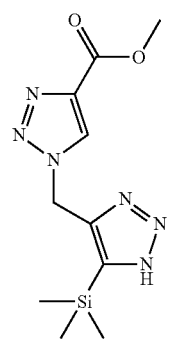 [SMILES: COC(=O)c1cn(Cc2nn[nH]c2[Si](C)(C)C)nn1]

Place methyl 1-(3-trimethylsilylprop-2-ynyl)triazole-4-carboxylate (240 mg, 1.01 mmoles) in a microwave reaction vessel and add dimethylformamide (6 mL) and water (6 mL). Add copper(II) sulfate pentahydrate (50.50 mg, 0.202 mmoles) and L-ascorbic acid sodium salt (400.67 mg, 2.02 mmoles). Degas the system bubbling nitrogen and sparging three times. Add azidotrimethylsilane (540.00 µL, 4.04 mmoles) and heat at 90° C. for 18 hours. Quench the reaction with water and extract three times with ethyl acetate. Wash one time with brine and dry over sodium sulfate, filter and concentrate under reduced pressure. The residue is purified by normal phase chromatography using

Preparation 13

Synthesis of 1-(1H-triazol-4-ylmethyl)triazole-4-carboxylic acid

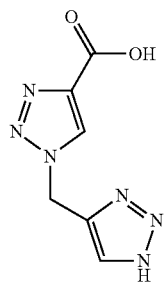 [SMILES: O=C(O)c1cn(Cc2c[nH]nn2)nn1]

Place methyl 1-[(5-trimethylsilyl-1H-triazol-4-yl)methyl]triazole-4-carboxylate (0.28 g, 1.00 mmoles), tetrahydrofuran (5.00 mL), lithium hydroxide (209.55 mg, 4.99 mmoles) and water (2.38 mL) in a round bottom flask and heat at 55° C. for 3 hours. Acidify the reaction mixture with 1 N hydrochloric acid and concentrate under reduced pressure until dry to give the title compound as a white solid (0.47 g, >100%). LCMS (m/z): 234.0 (M+40). $^1$H NMR (400 MHz, DMSO-$d_6$) ppm: 5.75 (s, 1H), 7.94 (bs, 1H), 8.67 (s, 1H), 15.33 (bs, 1H).

Preparation 14

Synthesis of methyl 3-(3-trimethylsilylprop-2-ynoxy)benzoate

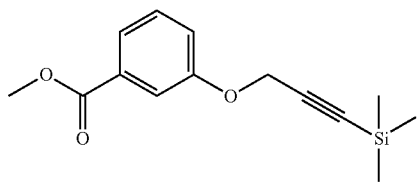

Place methyl 3-hydroxybenzoate (502.10 mg, 3.3 mmoles) and dimethylformamide (7.00 mL) in a round bottom flask. Cool the mixture to 0° C. Add sodium hydride (171.58 mg, 4.29 mmoles) portionwise and stir for 15 minutes. Add 3-bromoprop-1-ynyl(trimethyl)silane (700.34 µL, 4.95 mmoles) and stir for 18 hours. Quench the reaction with water and extract three times with ethyl acetate. Wash one time with brine and dry over sodium sulfate, filter and concentrate under reduced pressure. The residue is purified by normal phase chromatography using ethyl acetate/hexane to give the title compound (0.24 g, 28%). LCMS (m/z): 263.0 (M+1).

Preparation 15

Synthesis of methyl 3-[(5-trimethylsilyl-1H-triazol-4-yl)methoxy]benzoate

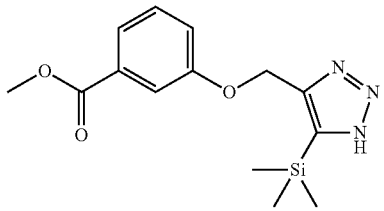 [SMILES: COC(=O)c1cccc(OCc2nn[nH]c2[Si](C)(C)C)c1]

Place methyl 3-(3-trimethylsilylprop-2-ynoxy)benzoate (234 mg, 0.89 mmoles) in a round bottom flask and add dimethylformamide (5.6 mL) and water (5 mL). Add copper (II) sulfate pentahydrate (44 mg, 0.18 mmoles) and L-ascorbic acid sodium salt (353 mg, 1.78 mmoles). Degas the system bubbling nitrogen and sparging three times. Add azidotrimethylsilane (0.475 mL, 3.57 mmoles) and heat at 90° C. for 18 hours. Quench the reaction with water and extract three times with ethyl acetate. Wash one time with brine and dry over sodium sulfate, filter and concentrate under reduced pressure. The residue is purified by normal phase chromatography using methanol/acetonitrile to give the title compound (0.27 g, 55%). LCMS (m/z): 306.0 (M+1).

Preparation 16

Synthesis of 3-(1H-triazol-4-ylmethoxy)benzoic acid

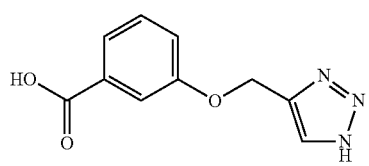 [SMILES: O=C(O)c1cccc(OCc2c[nH]nn2)c1]

Place methyl 3-[(4-trimethylsilyl-1H-triazol-5-yl)methoxy]benzoate (0.15 g, 0.49 mmoles), tetrahydrofuran (2 mL), lithium hydroxide (206 mg, 4.91 mmoles) and water (1 mL) in a round bottom flask and heat at 55° C. for 3 hours. Acidify the reaction mixture with 1 N hydrochloric acid and concentrate under reduced pressure until dry to give the title compound as a white solid (0.14 g, 70%). LCMS (m/z): 220.0 (M+40).

Preparation 17

Synthesis of methyl 3-(2-trimethylsilylethynyl)benzoate

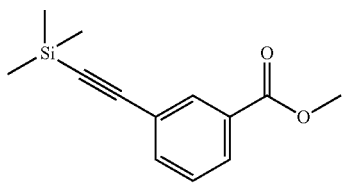

In a round bottom flask place methyl 3-bromobenzoate (1.88 g, 8.73 mmoles), triethylamine (10.00 mL, 71.74 mmoles), (trimethylsilyl)acetylene (1.48 mL, 10.49 mmoles), bis(triphenylphosphine)palladium(II) chloride (0.146 g, 0.205 mmoles), and copper(I) iodide (23 mg, 0.121 mmoles). The reaction mixture is heated at 90° for 18 hours. The reaction mixture is degassed and more (trimethylsilyl)acetylene (1.48 mL, 10.49 mmoles), methyl 3-bromobenzoate (1.88 g, 8.73 mmoles) and copper(I) iodide (23 mg, 0.121 mmoles) is added and the mixture is heated at 90° for 18 hours. Quench the reaction with 75 mL 1N hydrochloric acid and extract three times with ethyl acetate. Wash one time with brine and dry over sodium sulfate, filter and concentrate under reduced pressure. The residue is purified by normal phase chromatography using ethyl acetate/hexane to give the title compound (1.4 g, 69%). LCMS (m/z): 233.0 (M+1).

Preparation 18

Synthesis of 3-ethynylbenzoic acid

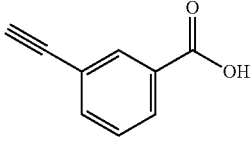

Place methyl 3-(2-trimethylsilylethynyl)benzoate (0.399 g, 1.55 mmoles) and tetrahydrofuran (3.68 mL) in a round bottom flask. Add lithium hydroxide (0.162 g, 3.86 mmoles) and water (3.68 mL) and heat at 50° C. Quench the reaction with 1.3 mL 5N hydrochloric acid and extract three times with ethyl acetate. Wash one time with brine and dry over sodium sulfate, filter and concentrate under reduced pressure to give the title compound (0.26 g, >100%). $^1$H NMR (400 MHz, DMSO-$d_6$) ppm: 4.39 (s, 3H), 7.50 (m, 2H), 7.70 (m, 1H), 7.94 (m, 1H) 13.22 (s, 1H).

Preparation 19

Synthesis of (3-ethynylphenyl)-[2-(indan-2-ylamino)-7,8-dihydro-5H-pyrido[4,3-d]pyrimidin-6-yl]methanone

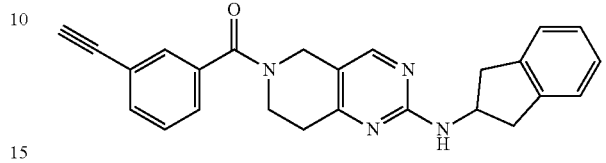

Place 3-ethynylbenzoic acid (259 mg, 1.78 mmoles), N-indan-2-yl-5,6,7,8-tetrahydropyrido[4,3-d]pyrimidin-2-amine (430 mg, 1.78 mmoles), 1-(3-dimethylaminopropyl)-3-ethylcarbodiimide hydrochloride (464 mg, 2.42 mmoles), and 4-pyridinamine, N,N-dimethyl (9.86 mg, 0.080 mmoles) in a round bottom flask and dissolve in dichloromethane (13 mL). Stir the reaction mixture for 1 hour at 25° C. Concentrate under reduced pressure. The residue is purified by normal phase chromatography using methanol/dichloromethane to give the title compound (0.64 g, 91%). LCMS (m/z): 395.2 (M+1).

Example 2

Synthesis of [2-(indan-2-ylamino)-7,8-dihydro-5H-pyrido[4,3-d]pyrimidin-6-yl]-[1-(3-methylimidazol-4-yl)pyrazol-4-yl]methanone

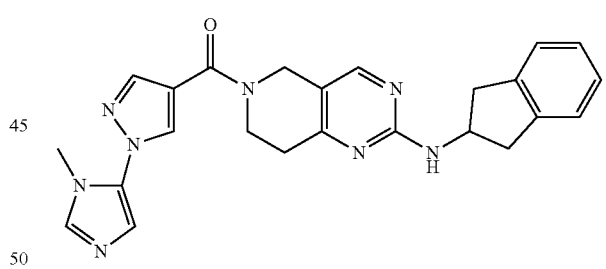

Place [2-(indan-2-ylamino)-7,8-dihydro-5H-pyrido[4,3-d]pyrimidin-6-yl]-(1H-pyrazol-4-yl)methanone (0.142 g, 0.40 mmoles), 5-bromo-1-methyl-imidazole (89 mg, 0.55 mmoles), cesium carbonate (257 mg, 0.79 mmoles), (1R, 2R)-diaminomethylcyclohexane (16 mg, 0.12 mmoles), and copper(I) iodide (7.50 mg, 0.039 mmoles) in a microwave reaction vessel. Add toluene (2 mL) and dimethylformamide (2 mL). The vessel is sealed and purged three times and heated at 110° C. for 48 hrs. The reaction is allowed to cool to room temperature and is quenched with water (2 mL). Extract three times with ethyl acetate. Dry over sodium sulfate, filter and concentrate under reduced pressure. The residue is purified by reverse phase chromatography to give the title compound (0.078 g, 0.42%). LCMS (m/z): 441.2 (M+1).

Example 3

Synthesis of [1-(3-imidazol-1-ylpropyl)pyrazol-4-yl]-[2-(indan-2-ylamino)-7,8-dihydro-5H-pyrido[4,3-d]pyrimidin-6-yl]methanone

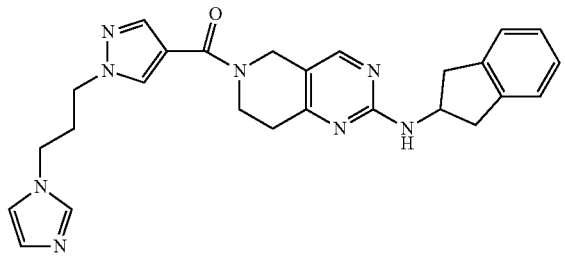 [SMILES: O=C(c1cnn(CCCn2ccnc2)c1)N1CCc2nc(NC3Cc4ccccc4C3)ncc2C1]

Place [2-(indan-2-ylamino)-7,8-dihydro-5H-pyrido[4,3-d]pyrimidin-6-yl]-(1H-pyrazol-4-yl)methanone (180 mg, 0.50 mmoles), cesium carbonate (507 mg, 1.56 mmoles), and sodium iodide (12.5 mg, 0.083 mmoles) in a round bottom flask. Add dimethylformamide (2.5 mL) and stir for 20 minutes. Add 1-(3-bromopropyl)imidazole hydrobromide (150.00 mg, 0.56 mmoles) dissolved in 2 mL of dimethylformamide. Quench the reaction with water and extract three times with ethyl acetate. Dry over sodium sulfate, filter and concentrate under reduced pressure. The residue is purified by normal phase chromatography using methanol/dichloromethane to give the title compound (0.073 g, 28%). LCMS (m/z): 469.0 (M+1).

Example 4

Synthesis of [1-(2-imidazol-1-ylethyl)imidazol-4-yl]-[2-(indan-2-ylamino)-7,8-dihydro-5H-pyrido[4,3-d]pyrimidin-6-yl]methanone

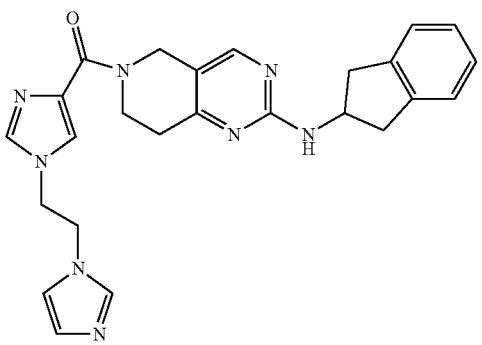 [SMILES: O=C(c1cn(CCn2ccnc2)cn1)N1CCc2nc(NC3Cc4ccccc4C3)ncc2C1]

Place 1H-imidazol-4-yl-[2-(indan-2-ylamino)-7,8-dihydro-5H-pyrido[4,3-d]pyrimidin-6-yl]methanone (200 mg, 0.55 mmoles) and cesium carbonate (506 mg, 1.55 mmoles) in a round bottom flask. Add dimethylformamide (2.5 mL) and stir for 20 minutes. Add (2-bromoethyl)-1H-imidazol-1-ium bromide (156 mg, 0.61 mmoles) and stir for 20 minutes. Quench the reaction with water and extract three times with 9:1 dichloromethane/methanol. Wash one time with brine and dry over sodium sulfate, filter and concentrate under reduced pressure. The residue is purified by reverse phase chromatography using to give the title compound (0.058 g, 23%). LCMS (m/z): 455.2 (M+1).

Example 5

Synthesis of [2-(indan-2-ylamino)-7,8-dihydro-5H-pyrido[4,3-d]pyrimidin-6-yl]-[1-(1H-triazol-4-ylmethyl)pyrrol-3-yl]methanone

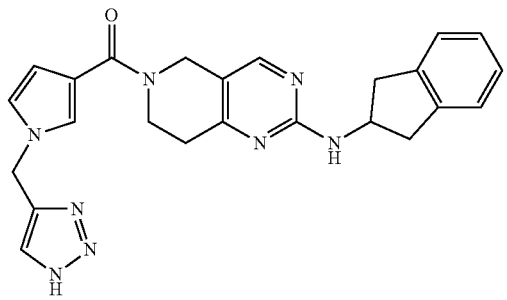 [SMILES: O=C(c1ccn(Cc2c[nH]nn2)c1)N1CCc2nc(NC3Cc4ccccc4C3)ncc2C1]

Place [2-(indan-2-ylamino)-7,8-dihydro-5H-pyrido[4,3-d]pyrimidin-6-yl]-(1-prop-2-ynylpyrrol-3-yl)methanone (140 mg, 0.35 mmoles) in a microwave reaction vessel and add dimethylformamide (3 mL) and water (4 mL). Add copper(II) sulfate pentahydrate (35 mg, 0.141 mmoles) and L-ascorbic acid sodium salt (279 mg, 1.41 mmoles). Degas the system bubbling nitrogen and sparging three times. Add azidotrimethylsilane (0.188 mL, 1.41 mmoles) and heat at 90° C. overnight. Quench the reaction with water and extract three times with ethyl acetate. Wash one time with brine and dry over sodium sulfate, filter and concentrate under reduced pressure. The residue is purified by normal phase chromatography using methanol/dichloromethane to give the title compound (0.083 g, 53%). LCMS (m/z): 441.2 (M+1).

Example 6

Synthesis of [2-(indan-2-ylamino)-7,8-dihydro-5H-pyrido[4,3-d]pyrimidin-6-yl]-[1-(1H-triazol-4-ylmethyl)triazol-4-yl]methanone

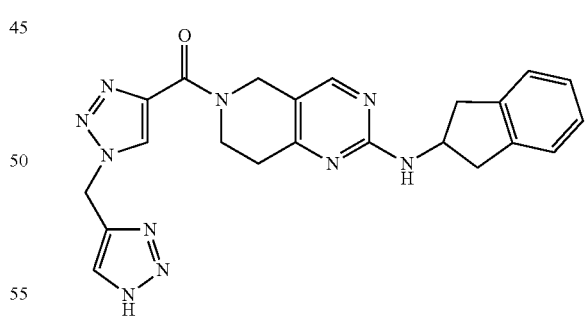

Place 1-(1H-triazol-4-ylmethyl)triazole-4-carboxylic acid (97 mg, 375 mmoles) and dimethyl sulfoxide (2 mL) in a round bottom flask. Add o-benzotriazol-1-yl-N,N,N',N'-tetramethyluronium tetrafluoroborate (240 mg, 0.725 mmoles) and diisopropylethylamine (450 μL, 2.58 mmoles) and stir for 15 minutes. Add N-indan-2-yl-5,6,7,8-tetrahydropyrido[4,3-d]pyrimidin-2-amine (0.100 g, 0.375 mmoles) and stir at 25° C. for 18 hours. Quench the reaction with water and extract three times with ethyl acetate. Wash one time with brine and dry over sodium sulfate, filter and concentrate under reduced pressure. The residue is purified by reverse phase to give the title compound (0.014 g, 8.4%). LCMS (m/z): 443.2 (M+1).

Example 7

Synthesis of [2-(indan-2-ylamino)-7,8-dihydro-5H-pyrido[4,3-d]pyrimidin-6-yl]-[3-(1H-triazol-5-yl)phenyl]methanone

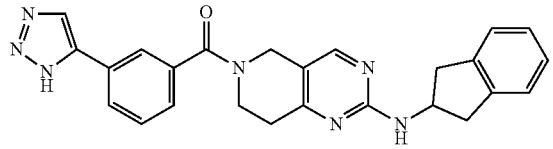 [SMILES: O=C(c1cccc(-c2cnn[nH]2)c1)N1CCc2nc(NC3Cc4ccccc4C3)ncc2C1]

Place (3-ethynylphenyl)-[2-(indan-2-ylamino)-7,8-dihydro-5H-pyrido[4,3-d]pyrimidin-6-yl]methanone (243 mg, 0.616 mmoles) in a microwave reaction vessel and add dimethylformamide (1.2 mL) and water (3.7 mL). Add copper(II) sulfate pentahydrate (31 mg, 0.123 mmoles) and L-ascorbic acid sodium salt (244 mg, 1.23 mmoles). Degas the system bubbling nitrogen and sparging three times. Add azidotrimethylsilane (0.33 mL, 2.46 mmoles) and heat at 90° C. for 2 hours. Quench the reaction with water and extract three times with 9:1 ethyl acetate/methanol. Dry over sodium sulfate, filter and concentrate under reduced pressure. The residue is purified by normal phase chromatography using methanol/ethyl acetate/hexane and then reverse phase chromatography to give the title compound (0.27 g, 33.0%). LCMS (m/z): 438.2 (M+1).

Preparation 20

Synthesis of 1-(1H-triazol-4-ylmethyl)pyrazole-4-carboxylic acid

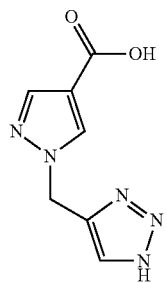 [SMILES: O=C(O)c1cnn(Cc2c[nH]nn2)c1]

Place ethyl 1-(1H-triazol-4-ylmethyl)pyrazole-4-carboxylate, (2.1 g, 7.16 mmoles) in a 100 mL round bottom flask and dissolve in tetrahydrofuran (30 mL) and water (15 mL). Add lithium hydroxide (1.50 g, 35.79 mmoles) and heat at 55° C. for 18 hours.

Dilute the reaction mixture with 5 N hydrochloric acid to pH 1-2. Remove the solvent under reduced pressure. Add ethanol and filter away the solid. Concentrate the filtrate under reduce pressure to give the title compound (3.01 g, >100%). LCMS (m/z): 194.0 (M+1).

Preparation 21

Synthesis of ethyl 1-(1H-triazol-4-ylmethyl)pyrazole-4-carboxylate

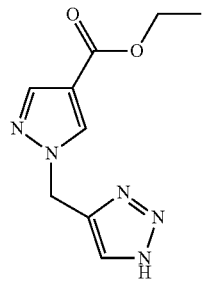 [SMILES: CCOC(=O)c1cnn(Cc2c[nH]nn2)c1]

Place ethyl 1-(3-trimethylsilylprop-2-ynyl)pyrazole-4-carboxylate (0.751 g, 3.00 mmoles) in a microwave vial and dissolve in dimethylformamide (12.00 mL) and water (18 mL). Add copper(II)sulfate pentahydrate (150 mg, 0.6 mmoles) and L-ascorbic acid sodium salt (1.19 g, 6.00 mmoles) and dimethylformamide (2 mL). Degas the reaction mixture three times. Add azidotrimethylsilane (1.60 mL, 12.00 mmoles) and heat at 90° C. for 15 hours. Cool the mixture to room temperature, extract three times with ethyl acetate and discard the aqueous phase. The organic layers are combined and washed one time with brine. Dry over sodium sulfate, filter and concentrate under reduced pressure. The residue is purified by flash silica gel chromatography with methanol/acetonitrile to give the title compound (0.5 g, 75%). LCMS (m/z): 222.0 (M+1).

Preparation 22

Synthesis of ethyl 1-(3-trimethylsilylprop-2-ynyl)pyrazole-4-carboxylate

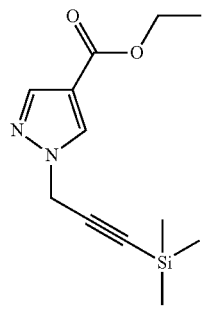 [SMILES: CCOC(=O)c1cnn(CC#C[Si](C)(C)C)c1]

Place ethyl 1H-pyrazole-4-carboxylate (700.7 mg, 5 mmoles) in a 50 mL round bottom flask and dissolve in dimethylformamide (11 mL). Cool the reaction mixture to 0° C. Add sodium hydride (180 mg, 4.5 mmoles) portion wise over 20 minutes. Stir the reaction mixture for 20 minutes and then add 3-bromoprop-1-ynyl(trimethyl)silane (0.92 mL, 6.5 mmoles) and stir for an additional 30 minutes. Quench the reaction mixture with water (20 mL) and extract three times with ethyl acetate and discard the aqueous phase. The organic layers are combined and washed one time with brine. Dry over sodium sulfate, filter and concentrate under reduced pressure. The residue is purified by flash silica gel chromatography with ethyl acetate/hexane to give the title compound (0.75 g, 60%). LCMS (m/z): 251.0 (M+1).

Example 8

Synthesis of [2-(indan-2-ylamino)-7,8-dihydro-5H-pyrido[4,3-d]pyrimidin-6-yl]-[1-(1H-triazol-4-ylm-ethyl)pyrazol-4-yl]methanone An alternative chemical name for the compound of Example 8 is [2-(2,3-dihydro-1H-inden-2-ylamino)-7,8-dihydropyrido[4,3-d]pyrimidin-6(5H)-yl][1-(1H-1,2,3-triazol-4ylmethyl)-1H-pyrazol-4-yl]methanone.

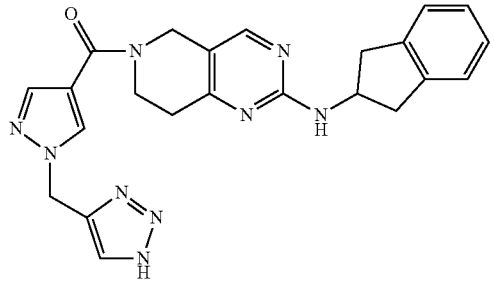 [SMILES: O=C(c1cnn(Cc2c[nH]nn2)c1)N1CCc2nc(NC3Cc4ccccc4C3)ncc2C1]

Place 1-(1H-triazol-4-ylmethyl)pyrazole-4-carboxylic acid (2.28 g 5.70 mmoles) in a 100 mL round bottom flask and dissolve in dimethyl sulfoxide (28.5 mL). Add diisopropylethylamine (6.8 mL, 39.2 mmoles), O-benzotriazol-1-yl-N,N,N',N'-tetramethyluronium tetrafluoroborate (3.5 g, 11.00 mmoles) and stir for 10 minutes. Add N-indan-2-yl-5,6,7,8-tetrahydropyrido[4,3-d]pyrimidin-2-amine (1.52 g, 5.70 mmoles) and stir the reaction mixture for 90 minutes. Quench the reaction with water (40 mL) and extract three times with 10% methanol/ethyl acetate and discard the aqueous phase. The organic layers are combined and washed one time with brine. Dry over sodium sulfate, filter and concentrate under reduced pressure. The residue is purified by reverse phase chromatography and crystallized with methanol/ethyl acetate/hexane to give the title compound (0.45 g, 18%). LCMS (m/z): 442.2 (M+1).

Preparation 23

Synthesis of (4-bromo-2-pyridyl)-[2-(indan-2-ylamino)-7,8-dihydro-5H-pyrido[4,3-d]pyrimidin-6-yl]methanone

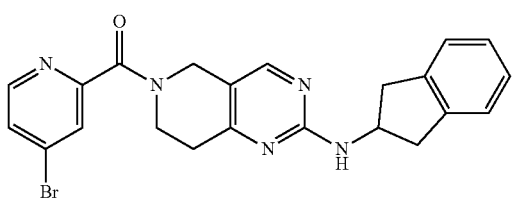 [SMILES: O=C(c1cc(Br)ccn1)N1CCc2nc(NC3Cc4ccccc4C3)ncc2C1]

Place N-indan-2-yl-5,6,7,8-tetrahydropyrido[4,3-d]pyrimidin-2-amine (2.66 g, 10 mmoles), 4-bromopyridine-2-carboxylic acid (2.24 g, 11.0 mmoles), 1-(3-dimethylaminopropyl)-3-ethylcarbodiimide hydrochloride (2.88 g, 15.0 mmoles), and 4-pyridinamine, N,N-dimethyl-(61 mg, 0.50 mmoles) in a 100 mL round bottom flask. Dissolve in dichloromethane (40 mL) and stir at room temperature for 18 hours. Concentrate and purify the residue by flash silica gel chromatography with acetonitrile/dichloromethane to give the title compound (2.9 g, 64%). LCMS (m/z): 452.0 (M+2).

Preparation 24

Synthesis of [2-(indan-2-ylamino)-7,8-dihydro-5H-pyrido[4,3-d]pyrimidin-6-yl]-[4-(2-trimethylsilyl-ethynyl)-2-pyridyl]methanone

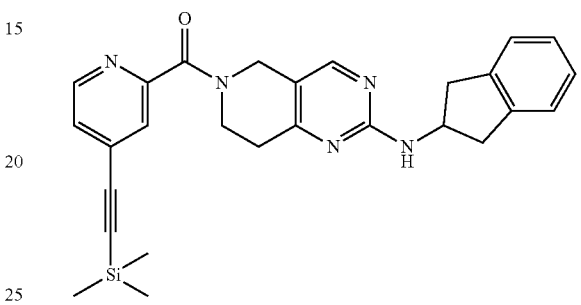

Place (4-bromo-2-pyridyl)-[2-(indan-2-ylamino)-7,8-dihydro-5H-pyrido[4,3-d]pyrimidin-6-yl]methanone (2.9 g, 6.44 mmoles), trimethylsilyl-acetylene (1.1 mL, 7.73 mmoles), triethylamine (16 mL, 116 mmoles), bis(triphenyl-phosphine)palladium(II) Chloride (219 mg, 0.31 mmoles) and copper(I) iodide (32 mg, 0.2 mmoles) in a 50 mL round bottom flask. Dissolve in dimethylformamide (32 mL) and degas the reaction mixture three times. Heat the reaction mixture at 65° C. for 18 hour. Cool the mixture to room temperature, dilute with water and extract three times with ethyl acetate and discard the aqueous phase. Combine and wash the organic layers one time with brine. Dry over sodium sulfate, filter and concentrate under reduced pressure. Purify the residue by flash silica gel chromatography with ethyl acetate/hexane to give the title compound (1.3 g, 43%). LCMS (m/z): 468.2 (M+1).

Preparation 25

Synthesis of (4-ethynyl-2-pyridyl)-[2-(indan-2-ylamino)-7,8-dihydro-5H-pyrido[4,3-d]pyrimidin-6-yl]methanone

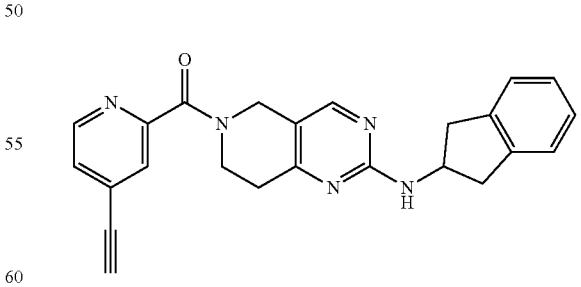

Place [2-(indan-2-ylamino)-7,8-dihydro-5H-pyrido[4,3-d]pyrimidin-6-yl]-[4-(2-trimethylsilylethynyl)-2-pyridyl]methanone (1.3 g, 2.78 mmoles) in a 50 mL round bottom flask. Dissolve in tetrahydrofuran (18 mL) and cool the reaction mixture to 0° C. Add 1N tetrabutylammonium fluoride (3.06 mL; 3.06 mmoles) and stir for 30 minutes.

Quench the reaction with water (40 mL) and extract three times with ethyl acetate and discard the aqueous phase. Combine and wash organic layers one time with brine. Dry over sodium sulfate, filter and concentrate under reduced pressure. Purify the residue by flash silica gel chromatography with methanol/ethyl acetate to give the title compound (0.89 g, 81%). LCMS (m/z): 396.0 (M+1).

example 9

Synthesis of [2-(indan-2-ylamino)-7,8-dihydro-5H-pyrido[4,3-d]pyrimidin-6-yl]-[4-(1H-triazol-5-yl)-2-pyridyl]methanone An alternative chemical name for the compound of Example 9 is [2-(2,3-dihydro-1H-inden-2-ylamino)-7,8-dihydropyrido[4,3-d]pyrimidin-6(5H)-yl][4-(1H-1,2,3-triazol-5yl)pyridine-2-yl]methanone.

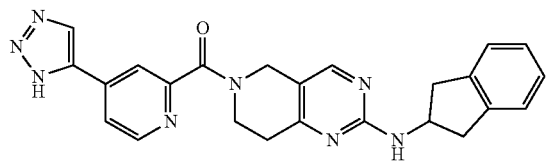 [SMILES: O=C(c1cc(-c2cnn[nH]2)ccn1)N1CCc2nc(NC3Cc4ccccc4C3)ncc2C1]

Place (4-ethynyl-2-pyridyl)-[2-(indan-2-ylamino)-7,8-dihydro-5H-pyrido[4,3-d]pyrimidin-6-yl]methanone (2.3 g, 4.92 mmoles) in a microwave vial and dissolve in dimethylformamide (29 mL) and water (29 mL). Add copper(II) sulfate pentahydrate (246 mg, 1 mmol) and L-ascorbic acid sodium salt (1.9 g, 9.8 mmoles) and dimethylformamide (15 mL). Degas the reaction mixture three times. Add azidotrimethylsilane (2.3 mL, 20 mmoles) dropwise over 20 minutes. Heat at 90° C. for 15 hours. Cool the mixture to room temperature, extract three times with ethyl acetate and discard the aqueous phase. The organic layers are combined and washed one time with brine. Dry over sodium sulfate, filter and concentrate under reduced pressure. The residue is purified by reverse phase chromatography to give the title compound (0.47 g, 22%). LCMS (m/z): 439.0 (M+1).

Preparation 26

Synthesis of (6-chloropyridazin-3-yl)-[2-(indan-2-ylamino)-7,8-dihydro-5H-pyrido[4,3-d]pyrimidin-6-yl]methanone

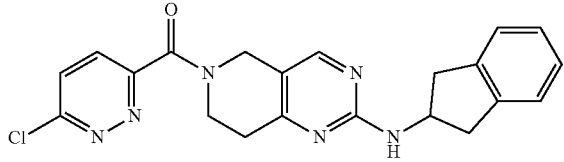 [SMILES: O=C(c1ccc(Cl)nn1)N1CCc2nc(NC3Cc4ccccc4C3)ncc2C1]

Stir a suspension of 6-chloropyridazine-3-carboxylic acid (1.93 g; 1.20 equiv; 12.17 mmoles), N-indan-2-yl-5,6,7,8-tetrahydropyrido[4,3-d]pyrimidin-2-amine (2.70 g; 1.00 equiv; 10.14 mmoles), and 1-(3-dimethylaminopropyl)-3-ethylcarbodiimide hydrochloride (2.14 g; 1.10 equiv; 11.16 mmoles) in dichloromethane (25 mL) for 30 minutes. Concentrate the reaction mixture under reduced pressure and purify the residue by column chromatography (0 to 5% methanol/methylene chloride) to provide the title compound (3.70 g; 90%). MS (m/z): 407 (M+1).

Preparation 27

Synthesis of tert-butyl 2-cyano-2-[6-[2-(indan-2-ylamino)-7,8-dihydro-5H-pyrido[4,3-d]pyrimidine-6-carbonyl]pyridazin-3-yl]acetate

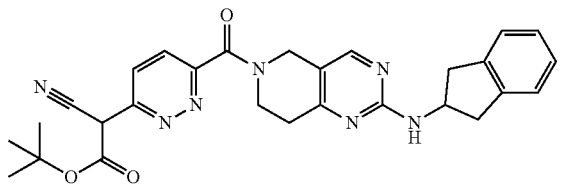 [SMILES: CC(C)(C)OC(=O)C(C#N)c1ccc(C(=O)N2CCc3nc(NC4Cc5ccccc5C4)ncc3C2)nn1]

Add t-butyl cyanoacetate (0.27 mL; 1.52 equiv; 1.83 mmoles) to a stirred suspension of sodium hydride (0.12 g; 2.50 equiv; 3.00 mmoles) in 1,4-dioxane (6.5 mL) at room temperature. After 1 hour, add (6-chloropyridazin-3-yl)-[2-(indan-2-ylamino)-7,8-dihydro-5H-pyrido[4,3-d]pyrimidin-6-yl]methanone (0.49 g; 1.00 equiv; 1.20 mmoles) and heat the resulting reaction mixture at 100° C. for 16 hours. Cool the reaction mixture to room temperature, partition between ethyl acetate and 0.5 M hydrochloric acid, and separate the layers. Dry the organic layer over anhydrous sodium sulfate, filter, and concentrate under reduced pressure to provide the title compound (0.61 g; 99%). MS (m/z): 512 (M+H).

Preparation 28

Synthesis of 2-[6-[2-(indan-2-ylamino)-7,8-dihydro-5H-pyrido[4,3-d]pyrimidine-6-carbonyl]pyridazin-3-yl]acetonitrile

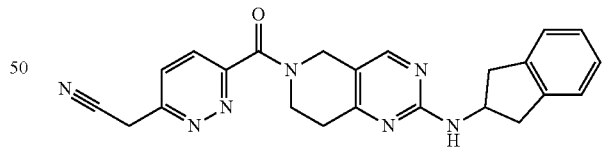

Add p-toluenesulfonic acid monohydrate (0.025 g; 0.11 equiv; 0.13 mmoles) to a stirred solution of tert-butyl 2-cyano-2-[6-[2-(indan-2-ylamino)-7,8-dihydro-5H-pyrido[4,3-d]pyrimidine-6-carbonyl]pyridazin-3-yl]acetate (0.61 g; 1.00 equiv; 1.19 mmoles) in toluene (8 mL) and heat to reflux for 3 hours, then cool to room temperature and filter. Dissolve the solid residue in methylene chloride (30 mL) and wash with saturated sodium bicarbonate, dry over anhydrous sodium sulfate, filter, and concentrate. Purify the residue by column chromatography (50 to 75% acetone/hexanes) to provide the title compound (0.255 g; 52%). MS (m/z): 412 (M+H).

Example 10

Synthesis of [2-(2,3-dihydro-1H-inden-2-ylamino)-7,8-dihydropyrido[4,3-d]pyrimidin-6(5H)-yl][6-(1H-tetrazol-5-ylmethyl)pyridazin-3-yl]methanone

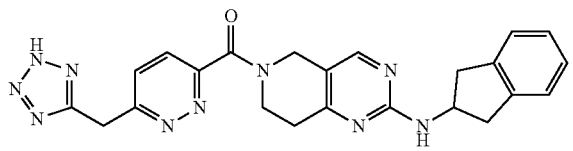 [SMILES: O=C(c1ccc(Cc2nn[nH]n2)nn1)N1CCc2nc(NC3Cc4ccccc4C3)ncc2C1]

Add azidotrimethylsilane (0.81 mL; 10 equiv; 6.08 mmoles) and dibutyloxostannane (0.042 g; 0.28 equiv; 0.17 mmoles) to a stirred suspension of 2-[6-[2-(indan-2-ylamino)-7,8-dihydro-5H-pyrido[4,3-d]pyrimidine-6-carbonyl]pyridazin-3-yl]acetonitrile (0.25 g; 1.00 equiv; 0.61 mmoles) in toluene (6 mL) and heat the resulting reaction mixture at 110° C. for 16 hours, then cool to room temperature and concentrate under reduced pressure. Purify the resulting residue by reverse phase column chromatography to afford the title compound (0.074 g; 27%): MS (m/z): 455 (M+H).

Preparation 29

Synthesis of [2-(indan-2-ylamino)-7,8-dihydro-5H-pyrido[4,3-d]pyrimidin-6-yl]-[6-(2-trimethylsilyl-ethynyl)pyridazin-3-yl]methanone

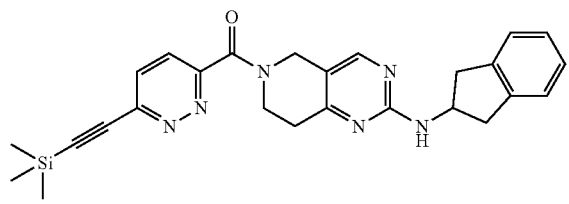 [SMILES: C[Si](C)(C)C#Cc1ccc(C(=O)N2CCc3nc(NC4Cc5ccccc5C4)ncc3C2)nn1]

Irradiate a microwave vial charged with a suspension of (6-chloropyridazin-3-yl)-[2-(indan-2-ylamino)-7,8-dihydro-5H-pyrido[4,3-d]pyrimidin-6-yl]methanone (0.505 g; 1.00 equiv; 1.24 mmoles), copper (I) iodide (0.014 g; 0.06 equiv; 0.073 mmoles), bis(triphenylphosphine)palladium(II) chloride (0.043 g; 0.05 equiv; 0.061 mmoles) and trimethylsilylacetylene (0.69 mL; 3.94 equiv; 4.90 mmoles) in dimethylformamide (0.9 mL) and triethylamine (10 mL) at 140° C. for 30 minutes. Partition the reaction mixture between ethyl acetate and 0.1 N hydrochloric acid and separate. Stir the organic layer was with SiliCycle (SiliaMetS Thiol) for 30 minutes, filter, and concentrate. Dissolve the residue in 50% acetone/hexanes and purify using a silica gel plug. Concentrate the filtrate under reduced pressure to afford the title compound (0.44 g; 76%): MS (m/z): 469 (M+H).

Preparation 30

Synthesis of [6-(2,2-dimethoxyethyl)pyridazin-3-yl]-[2-(indan-2-ylamino)-7,8-dihydro-5H-pyrido[4,3-d]pyrimidin-6-yl]methanone An alternative chemical name for the compound for Preparation 30 is (6-ethynylpyridazin-3-yl)-[2-(indan-2-ylamino)-7,8-dihydro-5H-pyrido[4,3-d]pyrimidin-6-yl]methanone.

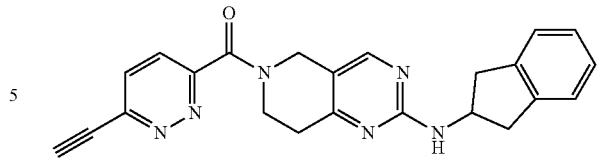

Stir a suspension of [2-(indan-2-ylamino)-7,8-dihydro-5H-pyrido[4,3-d]pyrimidin-6-yl]-[6-(2-trimethylsilylethynyl)pyridazin-3-yl]methanone (0.50 g; 1.00 equiv; 1.07 mmoles) and potassium carbonate (0.42 g; 2.8 equiv; 3.01 mmoles) in methanol (10 mL) for 15 minutes. Filter the reaction and concentrate under reduced pressure. Partition the residue between water and methylene chloride and separate the layers, then further extract the aqueous layer with methylene chloride (150 mL). Dry the combined organic extracts over anhydrous sodium sulfate, filter, and concentrate under reduced pressure. Purify the resulting residue by column chromatography (50% acetone/hexanes) to afford the title compound (0.082 g; 16%): MS (m/z): 397 (M+H).

Example 11

Synthesis of [2-(2,3-dihydro-1H-inden-2-ylamino)-7,8-dihydropyrido[4,3-d]pyrimidin-6(5H)-yl][6-(1H-1,2,3-triazol-5-yl)pyridazin-3-yl]methanone

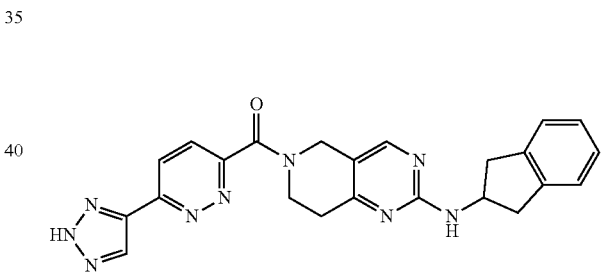

Degas and backfill (2x) a stirred suspension of (6-ethynylpyridazin-3-yl)-[2-(indan-2-ylamino)-7,8-dihydro-5H-pyrido[4,3-d]pyrimidin-6-yl]methanone (0.082 g; 1.00 equiv; 0.21 mmoles), copper(II)sulfate pentahydrate (0.005 g; 0.1 equiv; 0.020 mmoles), and L-ascorbic acid sodium salt (0.012 g; 0.3 equiv; 0.061 mmoles) in dimethylformamide (1 mL) and water (1 mL). Add azidotrimethylsilane (0.05 mL; 1.8 equiv; 0.375 mmoles) and heat the resulting reaction mixture at 90° C. for 1 hour. Cool the reaction mixture to ambient temperature, partition between 0.1 N hydrochloric acid and ethyl acetate, and separate. Further extract the aqueous layer with ethyl acetate (2x50 mL). Wash the combined organic extracts with brine (2x50 mL), dry over anhydrous sodium sulfate, filter, and concentrate under reduced pressure. Purify the residue by reverse phase column chromatography to afford the title compound (0.031 g; 35%). MS (m/z): 440 (M+H).

Preparation 31

Synthesis of (5-bromo-3-pyridyl)-[2-(indan-2-ylamino)-7,8-dihydro-5H-pyrido[4,3-d]pyrimidin-6-yl]methanone

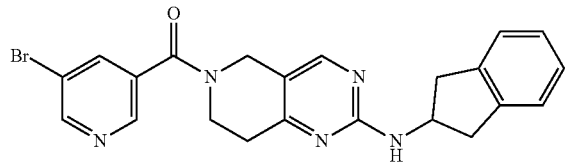 [SMILES: O=C(c1cncc(Br)c1)N1CCc2nc(NC3Cc4ccccc4C3)ncc2C1]

Stir a suspension of 5-bromonicotinic acid (0.91 g; 1.20 equiv; 4.51 mmoles), N-indan-2-yl-5,6,7,8-tetrahydropyrido[4,3-d]pyrimidin-2-amine (1.00 g; 1.00 equiv; 3.75 mmoles), and 1-(3-dimethylaminopropyl)-3-ethylcarbodiimide hydrochloride (0.791 g; 1.1 equiv; 4.13 mmoles) in dichloromethane (9 mL) for thirty minutes, then concentrate the reaction mixture under reduced pressure. Purify the crude residue by column chromatography (0 to 5% methanol/dichloromethane) to afford the title compound (1.145 g; 68%) as a white solid. MS (m/z): 450, 452 (M, M+2H).

Preparation 32

Synthesis of [2-(indan-2-ylamino)-7,8-dihydro-5H-pyrido[4,3-d]pyrimidin-6-yl]-[5-(2-trimethylsilylethynyl)-3-pyridyl]methanone

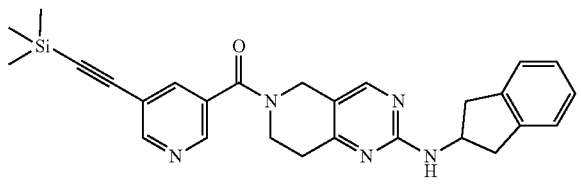 [SMILES: C[Si](C)(C)C#Cc1cncc(C(=O)N2CCc3nc(NC4Cc5ccccc5C4)ncc3C2)c1]

Irradiate a 20 mL microwave vial containing (5-bromo-3-pyridyl)-[2-(indan-2-ylamino)-7,8-dihydro-5H-pyrido[4,3-d]pyrimidin-6-yl]methanone (1.47 g; 1.00 equiv; 2.45 mmoles), bis(triphenylphosphine)palladium(II) chloride (0.086 g; 0.05 equiv; 0.12 mmoles), copper(I) iodide (0.024 g; 0.05 equiv; 0.12 mmoles), triethylamine (1.42 mL; 4.15 equiv; 10.16 mmoles), (trimethylsilyl)acetylene (2.42 mL; 7.0 equiv; 17.1 mmoles), and dimethylformamide (2.45 mL) at 120° C. for 50 minutes. Dilute the reaction mixture in ethyl acetate (75 mL) and add SiliaMetS thiol (1.381 g), then allow the reaction mixture to stir at ambient temperature for 16 hours. Filter the mixture and then wash the organics with lithium chloride solution (5%, 2×) and brine. Dry the organics over anhydrous sodium sulfate, filter, and concentrate. Purify the residue by column chromatography (30% acetone/hexanes) to afford the title compound (0.852 g; 74%) as an orange-brown foam. MS (m/z): 468 (M+H).

Preparation 33

Synthesis of (5-ethynyl-3-pyridyl)-[2-(indan-2-ylamino)-7,8-dihydro-5H-pyrido[4,3-d]pyrimidin-6-yl]methanone

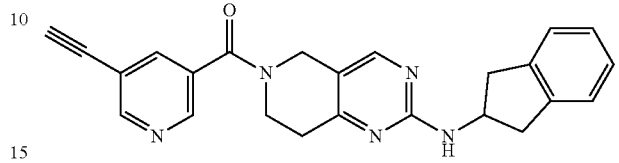

Stir a solution of [2-(indan-2-ylamino)-7,8-dihydro-5H-pyrido[4,3-d]pyrimidin-6-yl]-[5-(2-trimethylsilylethynyl)-3-pyridyl]methanone (0.852 g; 1.00 equiv; 1.82 mmoles) and potassium carbonate (0.76 g; 3.0 equiv; 5.47 mmoles) in methanol (5 mL) and dichloromethane (10 mL) at ambient temperature for 15 minutes, then concentrate the reaction mixture under reduced pressure. Dissolve the residue in ethyl acetate and wash with water. Dry the organic extracts over anhydrous sodium sulfate, filter, and concentrate to afford the title compound (0.753 g; >95%) as a solid. The material is used in the next step without further purification. MS (m/z): 396 (M+H).

Example 12

Synthesis of [2-(2,3-dihydro-1H-inden-2-ylamino)-7,8-dihydropyrido[4,3-d]pyrimidin-6(5H)-yl][5-(1H-1,2,3-triazol-5-yl)pyridin-3-yl]methanone

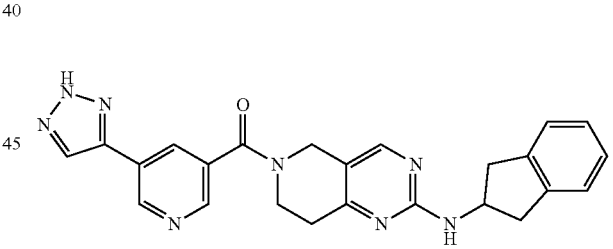

Degas and backfill (nitrogen gas) twice a solution containing (5-ethynyl-3-pyridyl)-[2-(indan-2-ylamino)-7,8-dihydro-5H-pyrido[4,3-d]pyrimidin-6-yl]methanone (0.72 g; 1.00 equiv; 1.82 mmoles), copper(II)sulfate pentahydrate (0.023 g; 0.05 equiv; 0.091 mmoles) and L-ascorbic acid sodium salt (0.072 g; 0.2 equiv; 0.36 mmoles) in dimethylformamide (1.8 mL) and water (1.8 mL). Add azidotrimethylsilane (0.36 mL; 1.5 equiv; 2.73 mmoles), and heat the reaction mixture to 90° C. for 2 hours. Cool the reaction mixture to room temperature and dilute with ethyl acetate and 50% saturated sodium chloride. Extract the aqueous layers were extracted with 3:1 chloroform: isopropanol. Dry the combined organic layers over anhydrous sodium sulfate, filter, and concentrate. Triturate the residue with methanol and ethyl acetate to afford the title compound (0.173 g; 22%) as an off-white solid. MS (m/z): 439 (M+H).

Preparation 34

Synthesis of 1H-imidazol-4-yl-[2-(indan-2-ylamino)-7,8-dihydro-5H-pyrido[4,3-d]pyrimidin-6-yl]methanone

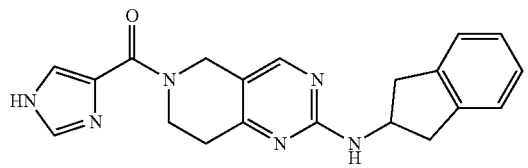 [SMILES: O=C(c1c[nH]cn1)N1CCc2nc(NC3Cc4ccccc4C3)ncc2C1]

Stir a mixture N-indan-2-yl-5,6,7,8-tetrahydropyrido[4,3-d]pyrimidin-2-amine (1.00 g; 1.00 equiv; 3.75 mmoles), 1H-imidazole-4-carboxylic acid (0.46 g; 1.10 equiv; 4.10 mmoles), 1-(3-dimethylaminopropyl)-3-ethylcarbodiimide hydrochloride (0.79 g; 1.10 equiv; 4.12 mmoles), 1-hydroxybenzotriazole hydrate (0.63 g; 1.10 equiv; 4.11 mmoles), and triethylamine (1.6 mL; 3.1 equiv; 11.48 mmoles) in dimethylformamide (12.5 mL) at room temperature overnight. Partition the solution between ethyl acetate and 5% lithium chloride solution and separate the layers, then further extract the aqueous layer with ethyl acetate. Dry the combined organic extracts over anhydrous sodium sulfate, filter, and concentrate under reduced pressure. Purify the crude residue by column chromatography (0 to 20% methanol/dichloromethane) to afford the title compound (0.842 g; 62%) as an off white solid. MS (m/z): 361 (M+H).

Example 13

Synthesis of [2-(2,3-dihydro-1H-inden-2-ylamino)-7,8-dihydropyrido[4,3-d]pyrimidin-6(5H)-yl][1-(1H-1,2,3-triazol-5-ylmethyl)-1H-imidazol-4-yl]methanone

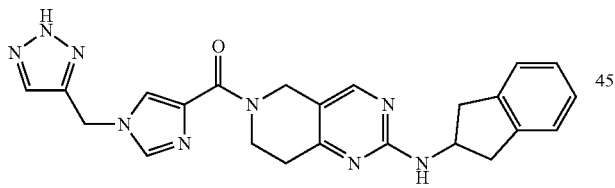

Add portion wise over 5 minutes sodium hydride (0.22 g; 2.00 equiv; 5.55 mmoles) to a 0° C. solution of 1H-imidazol-4-yl-[2-(indan-2-ylamino)-7,8-dihydro-5H-pyrido[4,3-d]pyrimidin-6-yl]methanone (1.00 g; 1.00 equiv; 2.77 mmoles) in tetrahydrofuran (10 mL) and stir for 15 minutes. Allow the mixture to warm to ambient temperature and add propargyl bromide (0.46 mL; 1.5 equiv; 4.16 mmoles). Stir the mixture was stirred at ambient temperature for 16 hours. Add methanol (1 mL) and concentrate the mixture. Purify the residue by column chromatography (0 to 5% methanol/dichloromethane) to afford the intermediate N-alkyl imidazole as a mixture of N-propargylic (0.697 g, 63%) and N-allenic isomers (0.123 g, 11%).

These products are combined and added to a solution of copper(II)sulfate pentahydrate (0.024 g; 0.05 equiv; 0.096 mmoles) in dimethylformamide (16.4 mL) and water (4 mL). Degas the system and backfill with nitrogen 3 times, then add L-ascorbic acid sodium salt (0.090 mg; 0.23 equiv; 0.45 mmoles). Add azidotrimethylsilane (0.40 mL; 1.50 equiv; 3.00 mmoles) and heat the reaction mixture at 90° C. for 16 hours. Partition the mixture between water and 3:1 chloroform:isopropyl alcohol and separate. Further extract the aqueous layer 3 times with 3:1 chloroform:isopropyl alcohol. Dry the combined organics over anhydrous sodium sulfate, filter, and concentrate in vacuo. Purify the product by reverse phase chromatography to afford the title compound (0.035 g; 5%) as a white solid. MS (m/z): 442 (M+H).

Preparation 35

Synthesis of (4-bromo-2-pyridyl)-[2-(indan-2-ylamino)-7,8-dihydro-5H-pyrido[4,3-d]pyrimidin-6-yl]methanone

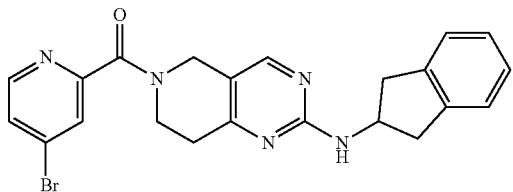 [SMILES: O=C(c1cc(Br)ccn1)N1CCc2nc(NC3Cc4ccccc4C3)ncc2C1]

Place N-indan-2-yl-5,6,7,8-tetrahydropyrido[4,3-d]pyrimidin-2-amine (2.66 g, 10 mmoles), 4-bromopyridine-2-carboxylic acid (2.24 g, 11.00 mmoles), 1-(3-dimethylaminopropyl)-3-ethylcarbodiimide hydrochloride (2.88 g, 15.00 mmoles), and 4-pyridinamine, N,N-dimethyl-(61.08 mg, 0.500 mmoles) in a 100 mL round bottom flask. Dissolve in dichloromethane (40.0 mL) and stir at room temperature for 18 hours. Concentrate and purify the residue by flash silica gel chromatography with acetonitrile/dichloromethane to give the title compound (2.9 g, 64%). LCMS (m/z): 452.0 (M+2).

Preparation 36

Synthesis of [2-(indan-2-ylamino)-7,8-dihydro-5H-pyrido[4,3-d]pyrimidin-6-yl]-[4-(2-trimethylsilylethynyl)-2-pyridyl]methanone

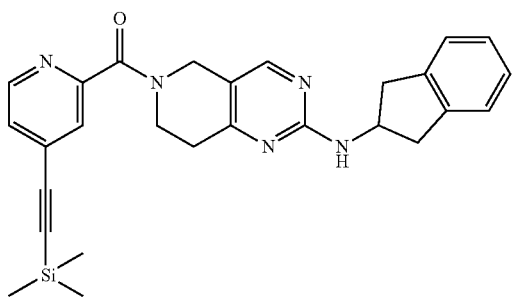 [SMILES: C[Si](C)(C)C#Cc1ccnc(C(=O)N2CCc3nc(NC4Cc5ccccc5C4)ncc3C2)c1]

Place (4-bromo-2-pyridyl)-[2-(indan-2-ylamino)-7,8-dihydro-5H-pyrido[4,3-d]pyrimidin-6-yl]methanone (2.9 g, 6.44 mmoles), trimethylsilyl-acetylene (1.1 mL, 7.73 mmoles), triethylamine (16 mL, 115.5 mmoles), bis(triphenylphosphine)palladium(II) chloride (219.15 mg, 0.31 mmoles) and copper(I) iodide (32 mg, 0.2 mmoles) in a 50 mL round bottom flask. Dissolve in dimethylformamide (32 mL) and degas the reaction mixture three times. Heat the reaction mixture at 65° C. for 18 hour. Cool the mixture to room temperature, dilute with water and extract three times with ethyl acetate and discard the aqueous phase. The organic layers are combined and washed one time with brine. Dry over sodium sulfate, filter and concentrate under reduced pressure. The residue is purified by flash silica gel chromatography with ethyl acetate/hexane to give the title compound (1.3 g, 43%). LCMS (m/z): 468.2 (M+1).

Preparation 37

Synthesis of (4-ethynyl-2-pyridyl)-[2-(indan-2-ylamino)-7,8-dihydro-5H-pyrido[4,3-d]pyrimidin-6-yl]methanone

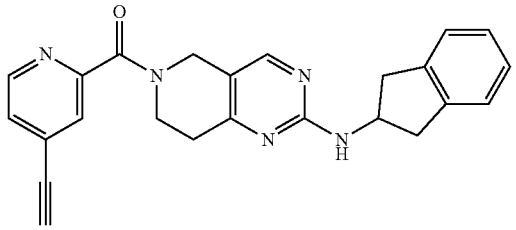 [SMILES: C#Cc1ccnc(C(=O)N2CCc3nc(NC4Cc5ccccc5C4)ncc3C2)c1]

Place [2-(indan-2-ylamino)-7,8-dihydro-5H-pyrido[4,3-d]pyrimidin-6-yl]-[4-(2-trimethylsilylethynyl)-2-pyridyl]methanone (1.3 g, 2.78 mmoles) in a 50 mL round bottom flask. Dissolve in tetrahydrofuran (18 mL; 15.89) and cool the reaction mixture to 0° C. Add 1M tetrabutylammonium fluoride (3.06 mL; 3.06 mmoles) and stir for 30 minutes. Quench the reaction with water (40 mL) and extract three times with ethyl acetate and discard the aqueous phase. The organic layers are combined and washed one time with brine. Dry over sodium sulfate, filter and concentrate under reduced pressure. The residue is purified by flash silica gel chromatography with methanol/ethyl acetate to give the title compound (0.89 g, 81%). LCMS (m/z): 396.0 (M+1).

Example 14

Synthesis of [2-(indan-2-ylamino)-7,8-dihydro-5H-pyrido[4,3-d]pyrimidin-6-yl]-[4-(1H-triazol-5-yl)-2-pyridyl]methanone An alternative chemical name for the compound of Example 14 is [2-(2,3-dihydro-1H-inden-2-ylamino)-7,8-dihydropryrido[4,3-d]pyrimidin-6(5H)-yl][4-(1H-1,2,3-triazol-5yl)pyridine-2-yl]methanone.

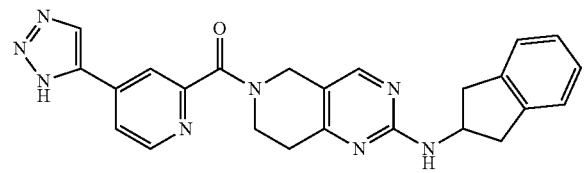 [SMILES: O=C(c1cc(-c2cnn[nH]2)ccn1)N1CCc2nc(NC3Cc4ccccc4C3)ncc2C1]

Place [2-(indan-2-ylamino)-7,8-dihydro-5H-pyrido[4,3-d]pyrimidin-6-yl]-[4-(2-trimethylsilylethynyl)-2-pyridyl]methanone (2.3 g, 4.92 mmoles) in a microwave vial and dissolve in dimethylformamide (29 mL) and water (29 mL). Add copper(II)sulfate pentahydrate (246 mg, 1.0 mmol) and L-ascorbic acid sodium salt (1.9 g, 9.8 mmoles) and dimethylformamide (15 mL). Degas the reaction mixture three times. Add azidotrimethylsilane (2.3 mL, 20 mmoles) dropwise over 20 minutes. Heat the mixture at 90° C. for 15 hours. Cool the mixture to room temperature, extract three times with ethyl acetate and discard the aqueous phase. The organic layers are combined and washed one time with brine. Dry over sodium sulfate, filter and concentrate under reduced pressure. The residue is purified by reverse phase chromatography to give the title compound (0.47 g, 22%). LCMS (m/z): 439.0 (M+1).

Preparation 38

Synthesis of 6-imidazol-1-ylpyridine-3-carboxylic acid

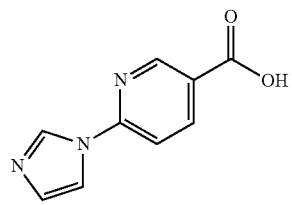 [SMILES: O=C(O)c1ccc(-n2ccnc2)nc1]

Place methyl 6-imidazol-1-ylpyridine-3-carboxylate (535 mg, 2.50 mmoles), tetrahydrofuran (12 mL), sodium hydroxide (780 mg, 3.75 mmoles) and methanol (10 mL) in a round bottom flask and heat at 50° C. for 3 hours. Acidify the reaction mixture with 1 N hydrochloric acid and concentrate under reduced pressure until dry. Suspend in methanol/dichloromethane, filter and concentrate to give the title compound as a white solid (0.47 g, 68%). LCMS (m/z): 190.0 (M+1).

Example 15

Synthesis of (6-imidazol-1-yl-3-pyridyl)-[2-(indan-2-ylamino)-7,8-dihydro-5H-pyrido[4,3-d]pyrimidin-6-yl]methanone

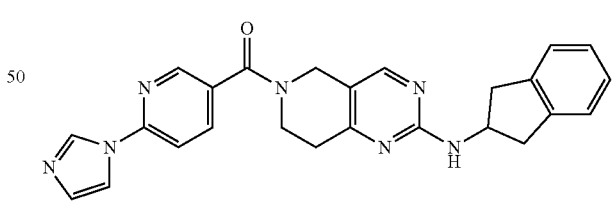

Place 6-imidazol-1-ylpyridine-3-carboxylic acid (125 mg, 0.66 mmoles), N-indan-2-yl-5,6,7,8-tetrahydropyrido[4,3-d]pyrimidin-2-amine (160 mg, 0.60 mmoles), 1-(3-dimethylaminopropyl)-3-ethylcarbodiimide hydrochloride (173 mg, 0.90 mmoles), and 4-pyridinamine, N,N-dimethyl (3.7 mg, 0.03 mmoles) in a round bottom flask and dissolve in dichloromethane (5 mL). Stir the reaction mixture for 18 hours at 25° C. Concentrate under reduced pressure to dryness. The residue is purified by reverse phase chromatography to give the title compound (0.049 g, 19%). LCMS (m/z): 438.0 (M+1).

Example 16

Synthesis of [4-(1H-imidazol-4-yl)phenyl]-[2-(indan-2-ylamino)-7,8-dihydro-5H-pyrido[4,3-d]pyrimidin-6-yl]methanone

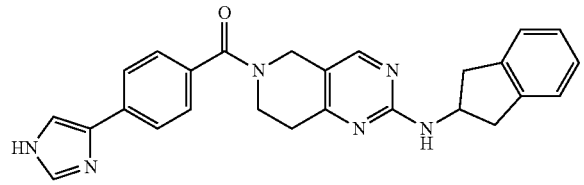 [SMILES: O=C(c1ccc(-c2c[nH]cn2)cc1)N1CCc2nc(NC3Cc4ccccc4C3)ncc2C1]

Place 4-(1H-imidazol-4-yl)benzoic acid (124 mg, 0.66 mmoles), N-indan-2-yl-5,6,7,8-tetrahydropyrido[4,3-d]pyrimidin-2-amine (160 mg, 0.60 mmoles), 1-(3-dimethylaminopropyl)-3-ethylcarbodiimide hydrochloride (173 mg, 0.90 mmoles), and 4-Pyridinamine, N,N-Dimethyl (3.7 mg, 0.03 mmoles) in a round bottom flask and dissolve in dichloromethane (5 mL). Stir the reaction mixture for 18 hours at 25° C. Concentrate under reduced pressure to dryness. The residue is purified by reverse phase chromatography to give the title compound (0.106 g, 40%). LCMS (m/z): 437.2 (M+1).

Preparation 39

Synthesis of (6-bromo-3-pyridyl)-[2-(indan-2-ylamino)-7,8-dihydro-5H-pyrido[4,3-d]pyrimidin-6-yl]methanone

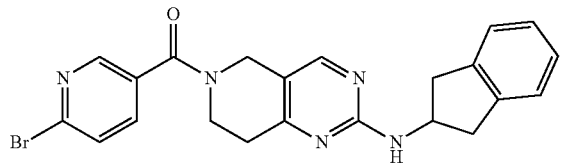 [SMILES: O=C(c1ccc(Br)nc1)N1CCc2nc(NC3Cc4ccccc4C3)ncc2C1]

Place 6-bromopyridine-3-carboxylic acid (224 mg, 1.10 mmoles), N-indan-2-yl-5,6,7,8-tetrahydropyrido[4,3-d]pyrimidin-2-amine (266 mg, 1.00 mmoles), 1-(3-dimethylaminopropyl)-3-ethylcarbodiimide hydrochloride (288 mg, 1.50 mmoles), and 4-pyridinamine, N,N-dimethyl (6.1 mg, 0.05 mmoles) in a round bottom flask and dissolve in dichloromethane (4 mL). Stir the reaction mixture for 18 hours at 25° C. Concentrate under reduced pressure. The residue is purified by normal phase chromatography using acetonitrile/dichloromethane to give the title compound (0.25 g, 55%). LCMS (m/z): 452.2 (M+1).

Preparation 40

Synthesis of [2-(indan-2-ylamino)-7,8-dihydro-5H-pyrido[4,3-d]pyrimidin-6-yl]-[6-(2-trimethylsilylethynyl)-3-pyridyl]methanone

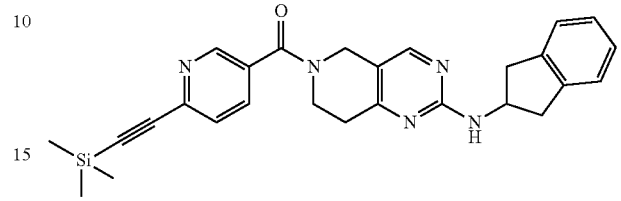

In a round bottom flask place (6-bromo-3-pyridyl)-[2-(indan-2-ylamino)-7,8-dihydro-5H-pyrido[4,3-d]pyrimidin-6-yl]methanone (260 mg, 0.57 mmoles), triethylamine (1.44 mL, 10.36 mmoles), (trimethylsilyl)acetylene (0.098 mL, 0.69 mmoles) bis(triphenylphosphine)palladium(II) chloride (9.8 mg, 0.014 mmoles), and copper(I) iodide (1.4 mg, 0.008 mmoles) in dimethylformamide (1.44 mL) and heat at 65° C. Quench the reaction with water and extract three times with ethyl acetate. Wash one time with brine and dry over sodium sulfate, filter and concentrate under reduced pressure. The residue is purified by normal phase chromatography using methanol/acetonitrile to give the title compound (0.17 g, 63%). LCMS (m/z): 468.2 (M+1).

Preparation 41

Synthesis of (6-ethynyl-3-pyridyl)-[2-(indan-2-ylamino)-7,8-dihydro-5H-pyrido[4,3-d]pyrimidin-6-yl]methanone

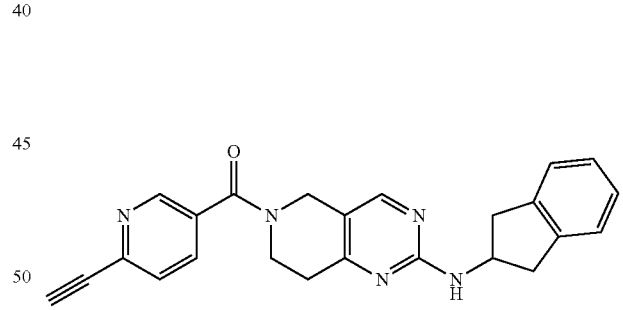

Place [2-(indan-2-ylamino)-7,8-dihydro-5H-pyrido[4,3-d]pyrimidin-6-yl]-[6-(2-trimethylsilylethynyl)-3-pyridyl]methanone (170 mg, 0.36 mmoles) in a round bottom flask. Add tetrahydrofuran (1 mL) and cool to 0° C. Add 1M tetra-N-butyl ammonium fluoride (0.40 mL, 0.40 mmoles) and stir for 30 minutes. Quench the reaction with water and extract three times with ethyl acetate. Wash one time with brine and dry over sodium sulfate, filter and concentrate under reduced pressure. The residue is purified by normal phase chromatography using methanol/ethyl acetate/hexane to give the title compound (0.087 g, 61%). LCMS (m/z): 396.2 (M+1).

Example 17

Synthesis of [2-(indan-2-ylamino)-7,8-dihydro-5H-pyrido[4,3-d]pyrimidin-6-yl]-[6-(1H-triazol-4-yl)-3-pyridyl]methanone

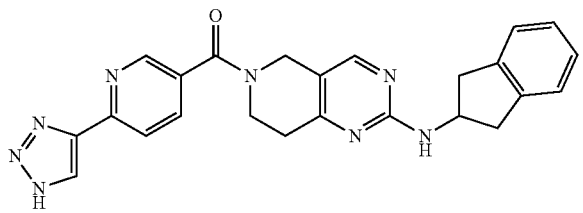 [SMILES: O=C(c1ccc(-c2c[nH]nn2)nc1)N1CCc2nc(NC3Cc4ccccc4C3)ncc2C1]

Place (6-ethynyl-3-pyridyl)-[2-(indan-2-ylamino)-7,8-dihydro-5H-pyrido[4,3-d]pyrimidin-6-yl]methanone (87 mg, 0.22 mmoles) in a microwave reaction vessel and add dimethylformamide (1.7 mL) and water (1.3 mL). Add copper(II) sulfate pentahydrate (11 mg, 0.044 mmoles) and L-ascorbic acid sodium salt (87 mg, 0.44 mmoles). Degas the system bubbling nitrogen and sparge three times. Add azidotrimethylsilane (0.117 mL, 0.88 mmoles) and heat at 90° C. for 2 hours. Quench the reaction with water and extract three times with 9:1 ethyl acetate/methanol. Dry over sodium sulfate, filter and concentrate under reduced pressure. The residue is purified by normal phase chromatography using ethyl acetate/hexane to give the title compound (0.043 g, 44%). LCMS (m/z): 439.2 (M+1).

Preparation 42

Synthesis of (5-bromo-2-pyridyl)-[2-(indan-2-ylamino)-7,8-dihydro-5H-pyrido[4,3-d]pyrimidin-6-yl]methanone

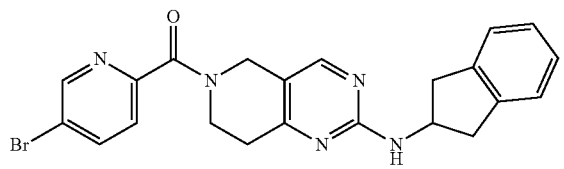 [SMILES: O=C(c1ccc(Br)cn1)N1CCc2nc(NC3Cc4ccccc4C3)ncc2C1]

Place 5-bromopyridine-2-carboxylic acid (224 mg, 1.10 mmoles), N-indan-2-yl-5,6,7,8-tetrahydropyrido[4,3-d]pyrimidin-2-amine (266 mg, 1.0 mmol), 1-(3-dimethylaminopropyl)-3-ethylcarbodiimide hydrochloride (288 mg, 1.50 mmoles), and 4-pyridinamine, N,N-dimethyl (6.1 mg, 0.050 mmoles) in a round bottom flask and dissolve in dichloromethane (4 mL). Stir the reaction mixture for 18 hours at 25° C. Concentrate under reduced pressure. The residue is purified by normal phase chromatography using acetonitrile/dichloromethane to give the title compound (0.34 g, 75%). LCMS (m/z): 452.2 (M+1).

Preparation 43

Synthesis of [2-(indan-2-ylamino)-7,8-dihydro-5H-pyrido[4,3-d]pyrimidin-6-yl]-[5-(2-trimethylsilylethynyl)-2-pyridyl]methanone

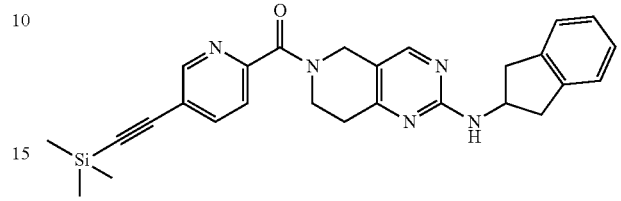

In a round bottom flask place (5-bromo-2-pyridyl)-[2-(indan-2-ylamino)-7,8-dihydro-5H-pyrido[4,3-d]pyrimidin-6-yl]methanone (0.34 g, 0.75 mmoles), triethylamine (1.89 mL, 13.54 mmoles), (trimethylsilyl)acetylene (0.128 mL, 0.91 mmoles) bis(triphenylphosphine)palladium(II) chloride (13 mg, 0.018 mmoles), and copper(I) iodide (1.9 mg, 0.010 mmoles) in dimethylformamide (2 mL) and heat at 90° C. Quench the reaction with water and extract three times with ethyl acetate. Wash one time with brine and dry over sodium sulfate, filter and concentrate under reduced pressure. The residue is purified by normal phase chromatography using ethyl acetate/hexane to give the title compound (0.25 g, 71%). LCMS (m/z): 468.2 (M+1).

Preparation 44

Synthesis of (5-ethynyl-2-pyridyl)-[2-(indan-2-ylamino)-7,8-dihydro-5H-pyrido[4,3-d]pyrimidin-6-yl]methanone

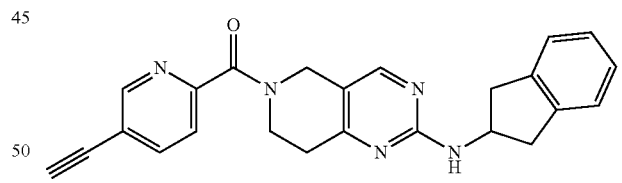

Place [2-(indan-2-ylamino)-7,8-dihydro-5H-pyrido[4,3-d]pyrimidin-6-yl]-[5-(2-trimethylsilylethynyl)-2-pyridyl]methanone (300 mg, 642 mmoles) in a round bottom flask. Add tetrahydrofuran (1.5 mL) and cool to 0° C. Add 1M tetra-N-butyl ammonium fluoride (0.71 mL, 0.71 mmoles) and stir for 30 minutes. Quench the reaction with water and extract three times with ethyl acetate. Wash one time with brine and dry over sodium sulfate, filter and concentrate under reduced pressure. The residue is purified by normal phase chromatography using methanol/ethyl acetate/hexane to give the title compound (0.18 g, 71%). LCMS (m/z): 396.2 (M+1).

Example 18

Synthesis of [2-(indan-2-ylamino)-7,8-dihydro-5H-pyrido[4,3-d]pyrimidin-6-yl]-[5-(1H-triazol-4-yl)-2-pyridyl]methanone

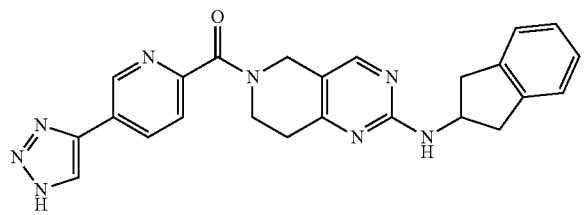 [SMILES: O=C(c1ccc(-c2c[nH]nn2)cn1)N1CCc2nc(NC3Cc4ccccc4C3)ncc2C1]

Place (5-ethynyl-2-pyridyl)-[2-(indan-2-ylamino)-7,8-dihydro-5H-pyrido[4,3-d]pyrimidin-6-yl]methanone (162 mg, 0.41 mmoles) in a microwave reaction vessel and add dimethylformamide (0.7 mL) and water (2.4 mL). Add copper(II) sulfate pentahydrate (20 mg, 0.082 mmoles) and L-ascorbic acid sodium salt (162 mg, 0.82 mmoles). Degas the system bubbling nitrogen and sparging three times. Add azidotrimethylsilane (0.218 mL, 1.64 mmoles) and heat at 90° C. for 2 hours. Quench the reaction with water and extract three times with 9:1 ethyl acetate/methanol. Dry over sodium sulfate, filter and concentrate under reduced pressure. The residue is purified by normal phase chromatography using methanol/ethyl acetate/hexane and then reverse phase chromatography to give the title compound (0.014 g, 8.0%). LCMS (m/z): 439.2 (M+1).

Inhibition of Autotaxin as Measured by Choline Release

The purpose of this assay is to detect autotaxin inhibition using a choline release assay.

Test compound (10 mM stocks in 100% DMSO) is serially diluted in 100% DMSO resulting in 10 concentrations of 100× inhibitor in half area 96 well plates (Corning 3992). Each of these 10 wells in 100% DMSO is diluted 1:33.33 in assay buffer in round bottom 96 well plates (Fisher 12565502) resulting in 3× concentrations in well containing 3% DMSO. The assay buffer is 50 mM Tris pH8.0, 5 mM KCl, 1 mM $CaCl_2$, 1 mM $MgCl_2$, 0.01% TRITON™ X-100 (Sigma T9284) and 0.01% fatty acid free bovine serum albumin (Sigma A8806). A 20 µl aliquot of each 3× test compound is then added to black flat bottom 96 well plates (Corning 3991) in singlicate. A 20 µl aliquot per well of 3× recombinant human autotaxin, (Echelon, E-4000) (full length human autotaxin with a C-terminal His tag transfected into 293E cells and purified via nickel chelate and size exclusion chromatography) is then added to every well except for the no enzyme control wells. A 20 µl aliquot per well of assay buffer is added to the no enzyme control wells. A 20 µl aliquot of a 3× cocktail containing choline oxidase (Sigma C5896), horseradish peroxidase (Sigma P8125), amplex ultrared (Invitrogen A36006) and the autotaxin substrate lysophosphatidylcholine (LPC) 16:0 (Avanti Polar Lipids 855675P) is added to each well while avoiding exposure to light. The final concentrations in the well of choline oxidase, horseradish peroxidase, amplex ultrared and LPC 16:0 are 0.4 units/ml, 4 units/ml, 40 µM and 30 µM respectively. The plate is then sealed with aluminum foil seals and incubated at 37° C. for 1 hour in a Labline Imperial III incubator. During this incubation, LPC is cleaved by autotaxin resulting in Lysophosphatidic Acid (LPA) 16:0 and choline. The choline that is released is oxidized by choline oxidase resulting in betaine and hydrogen peroxide. The hydrogen peroxide reacts with the horseradish peroxide and amplex ultrared to form the fluorescent molecule resorufin. The resorufin on the plates is measured with a SpectraMax Gemini EM fluorometer at excitation-emission wavelengths of 530-590 nm using SoftMax Pro 4.8 software. $IC_{50}$s are calculated using 4 parameter curve fits. The compound of Example 1 herein was tested essentially as described above. The IC50 is shown in Table 1. The exemplified compounds have an $IC_{50}$ of less than 30 nM.

TABLE 1

Inhibition of Autotaxin: Choline Release Assay

| Test Compound | $IC_{50}$ (nM) |
|---|---|
| Example 1 | <1.70 nM (n = 5) |
| Example 9 | <1.70 nM (n-5) |

The data in Table 1 illustrate that the compound of Example 1 inhibits autotaxin using the in vitro choline release assay.

Autotaxin Mediated Inhibition of LPA in the Presence of Human Plasma

The following assay is intended to measure autoxin mediated inhibition of LPA. This assay is a tool that can be used to identify autotaxin-mediated LPA inhibitor compounds when it is used to test compounds that have been identified as autotaxin inhibitors. LPA biosynthesis through autotaxin is believed to the source of LPA for $LPA_1$ mediated neuropathic pain. Makoto Inoue, et. al, "*Autotaxin, a synthetic enzyme of lysophosphatidic acid (LPA), mediates the induction of nerve-injured neuropathic pain*", Molecular Pain, 2008, 4:6. Inhibition of the autotaxin mediated LPA biosynthesis is supported by the results of this assay.

Units of plasma from healthy human female donors collected in sodium heparin (Lampire Biologicals) are pooled, aliquoted and stored at −80° C. On the day of assay, aliquots of the plasma are thawed and spun for 10 minutes at 3000 RPMs at 4° C. in a centrifuge to remove debris. A 90 µl aliquot of plasma is added to each well of a 96 well round bottom polypropylene plate. A 10 µL aliquot of 10× test compound containing 10% DMSO in assay buffer (50 mM Tris pH8.0, 5 mM KCl, 1 mM $CaCl_2$, 1 mM $MgCl_2$) is added to each well except for the control wells which contain no test compound. This results in 10 1× concentrations of test compound in singlicate with a final concentration of 1% DMSO in 90% plasma. A 10 µl aliquot of 10% DMSO in assay buffer without test compound is added to the 0 hour (n=8) and 3 hour no test compound controls (n=8) wells. A 10 µl aliquot of 500 mM ethylenediaminetetraacetic acid (EDTA) is added to each of the 0 hour no test compound control wells to chelate endogenous autotaxin. The entire contents of the 0 hour no test compound control wells are transferred to a new 96 well round bottom polypropylene plate and frozen at −80° C. The plate containing plasma +/− test compounds (minus the 0 hour no inhibitor control wells) is then incubated for 3 hours at 37° C. in a Robbins Scientific™ model 400 hybridization incubator while rocking at 14,000 RPMs. During this 3 hour incubation, lecithin cholesterol acyltransferases present in the plasma cleave phosphatidylcholine resulting in higher plasma levels of the autotaxin substrate lysophosphatidylcholine (LPC). The increased endogenous LPC levels are cleaved by endogenous autotaxin resulting in higher plasma concentrations of endogenous lysophosphatidic acid (LPA) (Nakamura et al, Clinical Biochemistry 40 (2007), 274-277). This increase in LPA in the 3 hour incubation can be inhibited by autotaxin inhibitors. Following the 3 hour incubation, 10 µl of 500 mM EDTA is added to all of the remaining wells (test compound containing wells and 3 hour no test compound control wells) to chelate the endogenous autotaxin. The entire contents of these wells are then added to the plate containing the 0 hour no test compound control plasma that had previously been stored at −80° C. (without thawing the 0 hour plasma). The plate is then re-covered with an aluminum foil seal and placed back at −80° C. until extraction for mass spec analysis. On the day of extraction, the plates are thawed on ice and 25 µl of plasma from each well is transferred to a 2 ml TrueTaper™ square 96 deep well plate (Analytical Sales and Products #968820). A 400 µl aliquot of extraction buffer (50% methanol, 49.9% acetonitrile, 0.1% acetic acid) containing LPA internal standards (50 ng/ml D5 deuterium LPA 16:0 and 50 ng/ml D5 deuterium LPA 18:0) is added to each well and the total LPA in each sample is determined by mass spec analysis. Percent inhibition of LPA is calculated according to the following formula:

100−(3 hour plasma+test compound−0 hour plasma no test compound control)/(3 hour plasma no test compound control−0 hour plasma no test compound control)×100

$$\% \text{ Inhibition of } LPA = \frac{100 - (3\,\text{hr test compound} - 0\,\text{hr no test compound control})}{(3\,\text{hr no test compound} - 0\,\text{hr no test compound control})} \times 100$$

IC$_{50}$ values are calculated using 4 parameter curve fitting. Results are expressed as the arithmetic mean +/− standard deviation; n=x. Results of this assay using compounds of this invention can show LPA inhibition that is dose dependent and statistically significant. The results of this assay can support that test compounds inhibit autotaxin mediated LPA biosynthesis.

IC$_{50}$ values are calculated using 4 parameter curve fitting. Results of this assay using compounds of this invention show autotaxin mediated LPA inhibition that is dose dependent.

TABLE 2

Autotaxin Mediated Inhibition of LPA in Human Plasma

| Test Compound | IC$_{50}$ (nM) |
| --- | --- |
| Example 1 | 5.4 (n = 5) (range 4.3 to 7.1) |
| Example 9 | 7.0 (n = 5) (range 6.1-9.3) |

The data in Table 2 demonstrate that the compound of Example 1 is an inhibitor of autotaxin mediated LPA in the presence of human plasma.

We claim:

1. A compound of the formula:

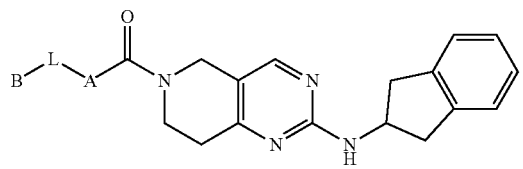

wherein

A is selected from the group consisting of

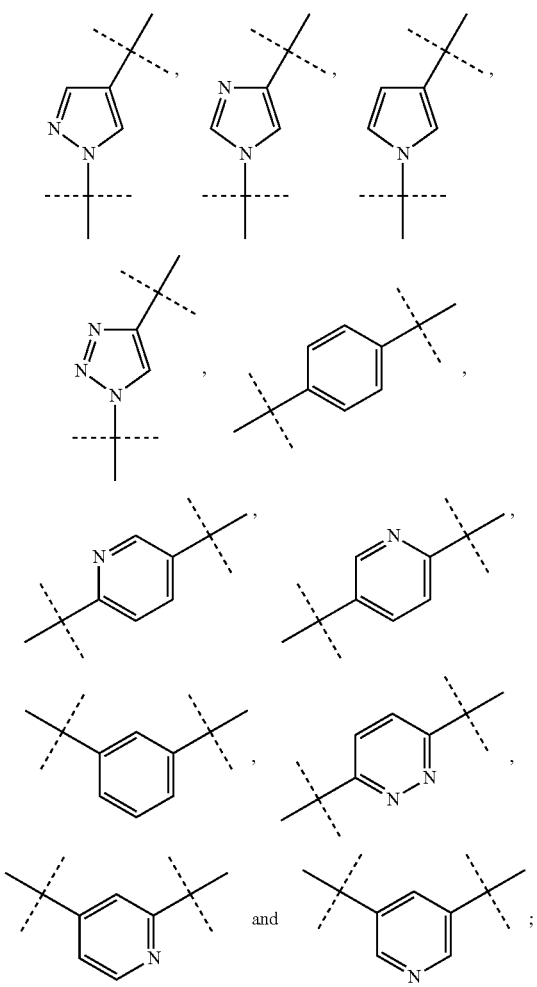

L is a bond or C$_1$-C$_3$ alkyl; and

B is selected from the group consisting of

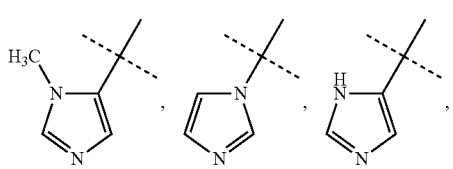

-continued

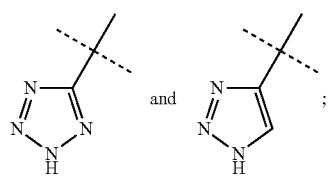

or a pharmaceutically acceptable salt thereof.

2. A compound or salt thereof, as claimed by claim 1 wherein L is selected from the group consisting of a bond or CH$_2$.

3. A compound or salt thereof, as claimed by claim 2 wherein B is selected from the group consisting of

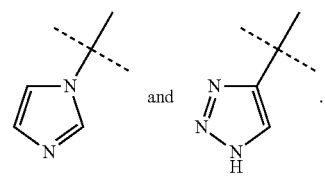

4. A compound or salt thereof as claimed by claim 3 wherein A is selected from the group consisting of

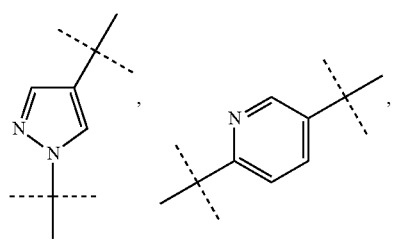

5. A compound or salt thereof, as claimed by claim 4 wherein A is selected from the group consisting of

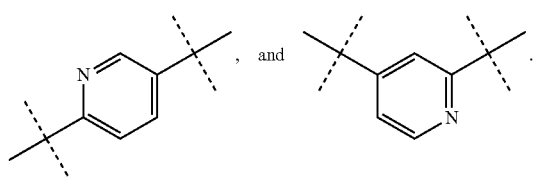

6. A compound or salt thereof, as claimed by claim 5 wherein B is

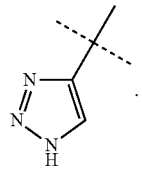

7. A compound or salt thereof, as claimed by claim 6 wherein A is

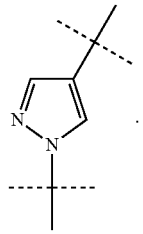

8. A compound or salt thereof, as claimed by claim 6 wherein L is CH$_2$.

9. A compound or salt thereof as claimed by claim 8 wherein A is

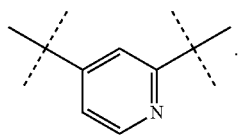

10. A compound or salt thereof as claimed by claim 7 wherein L is a bond.

11. A compound of Formula II, as claimed by claim 1

II

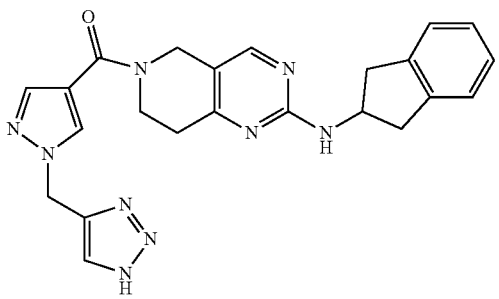

or a pharmaceutically acceptable salt thereof.

12. A compound of the formula III

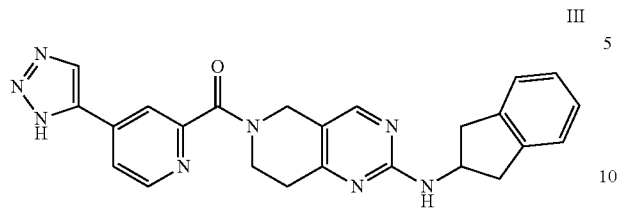

or a pharmaceutically acceptable salt thereof.

13. A pharmaceutical composition comprising a compound or a pharmaceutically acceptable salt thereof, according to claim 1, and one or more pharmaceutically acceptable carriers, diluents, or excipients.

14. A method of treating pain associated with osteoarthritis in a patient, comprising administering to a patient in need thereof, an effective amount of a compound according to claim 1, or a pharmaceutically acceptable salt thereof.

* * * * *

UNITED STATES PATENT AND TRADEMARK OFFICE
CERTIFICATE OF CORRECTION

PATENT NO.         : 9,550,774 B2                                    Page 1 of 1
APPLICATION NO.    : 14/761009
DATED              : January 24, 2017
INVENTOR(S)        : Thomas John Bleisch et al.

It is certified that error appears in the above-identified patent and that said Letters Patent is hereby corrected as shown below:

In the Claims

In Claim 4, delete " 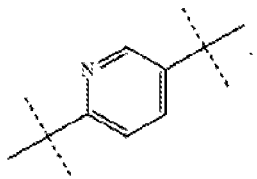 " and insert -- 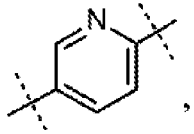 --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*